United States Patent [19]

Marra et al.

[11] Patent Number: 5,089,274
[45] Date of Patent: Feb. 18, 1992

[54] USE OF BACTERICIDAL/PERMEABILITY INCREASING PROTEIN OR BIOLOGICALLY ACTIVE ANALOGS THEREOF TO TREAT ENDOTOXIN-RELATED DISORDERS

[75] Inventors: Marian N. Marra, San Mateo; Randal W. Scott, Sunnyvale, both of Calif.

[73] Assignee: INCYTE Pharmaceuticals, Inc., Palo Alto, Calif.

[21] Appl. No.: 468,696

[22] Filed: Jan. 22, 1990

Related U.S. Application Data

[63] Continuation-in-part of Ser. No. 310,842, Feb. 14, 1989, abandoned.

[51] Int. Cl.$^5$ .............................................. A61K 35/14
[52] U.S. Cl. ........................................ 424/534; 514/2; 514/21; 530/829
[58] Field of Search .................... 424/534; 512/2, 21; 530/829

[56] References Cited

FOREIGN PATENT DOCUMENTS 0272489  6/1988  European Pat. Off.
8802700  8/1988  World Int. Prop. O.
9000837  2/1990  World Int. Prop. O.

OTHER PUBLICATIONS

Weiss et al., "Purification & Characterization . . . ", J. Biol. Chem. 253(8): 2664–2672, 1978.
Weiss et al., "The Role of Lipopolysaccharides . . . ", J. Immunol. 132(6): 3109–15, 1984.
Weiss et al., "Cellular & Subcellular . . . ", BA83(9): 86173, 1987.
Doi et al., "A 25-KDa NH$_2$-Terminal Fragment . . . ", J. Biol. Chem. 262(31): 14891–94, 1987.
Tobias et al., "A Family of . . . ", J. Biol. Chem. 263(27): 13479–81, 1988.
Elsbach et al., "Separation and Purification . . . ", J. Biol. Chem. 254(21): 11000–11009, 1979.
M. N. Marra, et al. (1990) J. Immunol., 144:662–666.
P. Elsbach, et al. (1988) Bacteria-Host Cell Interaction, pp. 47–60.
P. Gray, et al. (1988) Clinical Research, 36(3):620A.
P. Gray, et al. (1989) The Journal of Biological Chemistry 264(16):9505.
J. Weiss, et al. (1982) The American Society of Clinical Investigation, Inc. 69:959.
J. Weiss, et al. (1985) The American Society of Clinical Investigation, Inc. 76:206.
S. Leong, et al. J. Cell Biochem. Suppl. 13:66 (1989).
J. Weiss, et al. Infection and Immunity, 38:1149–1153 (1982).
K. Muello, et al. Clinical Research, 31:371A.
J. Weiss, et al. J. Clin. Invest., 71:540–549 (1983).
W. M. Shafer, et al. Infection and Immunity, 45:29–35 (1984).
C. J. Hovde, et al. Infection and Immunity, 54:142–148 (1986).
J. Weiss, et al. Infection and Immunity, 51:594–599 (1986).
J. K. Spitznagel, et al. J. Immunol., 139:1291–1296 (1987).
M. M. Shafer, et al. Infection and Immunity, 55:1536–1539 (1987).
G. I. Veld, et al. Infection and Immunity, 56:1203–1208 (1988).
M. M. Farley, et al. Infection and Immunity, 56:1589–1592 (1988).
B. A. Mannion et al., J. Immunol. 142:2807–2812 (1989).
J. Weiss, et al. (1985) ASCI Metabolism, 33(2):567(A).
B. A. Mannion et al., J. Clin. Invest. 85:853–860 (1990).
A. H. Pereira, et al., Blood 76:825–834 (1990).
R. R. Schumann, et al. Science 249:1429–1431 (1990).

*Primary Examiner*—Douglas W. Robinson
*Assistant Examiner*—Jean C. Witz
*Attorney, Agent, or Firm*—John P. White

[57] ABSTRACT

The present invention provides a method of inhibiting lipopolysaccharide (LPS)-mediated stimulation of cells. This method comprises contacting the cells, in the presence of a cell-stimulating amount of lipopolysaccharide, with Bactericidal/Permeability Increasing Protein (BPI) in an amount effective to inhibit cell stimulation.

25 Claims, 20 Drawing Sheets

FIGURE 1
A. LPS STIMULATION OF GRANULOCYTE CR1
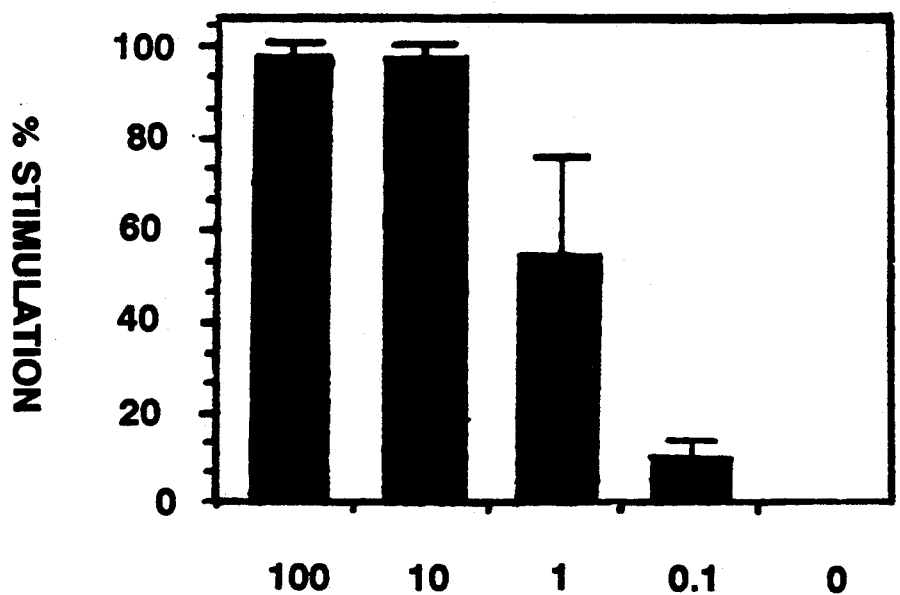
B. NEUTRALIZATION OF LPS BY CRUDE AZUROPHIL EXTRACT
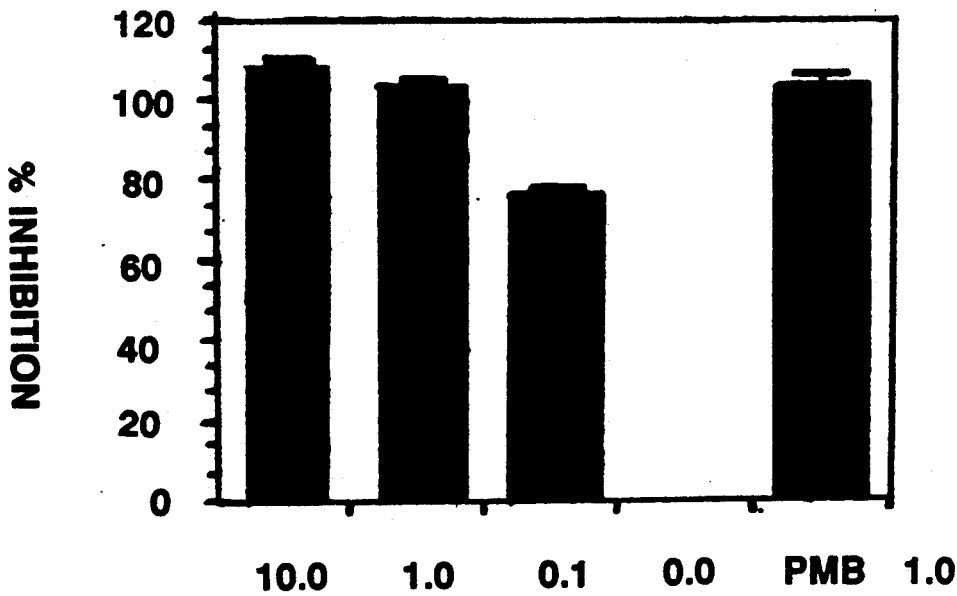

FIGURE 2
LPS INHIBITION BY RPLC PURIFIED AZUROPHIL GRANULE EXTRACT
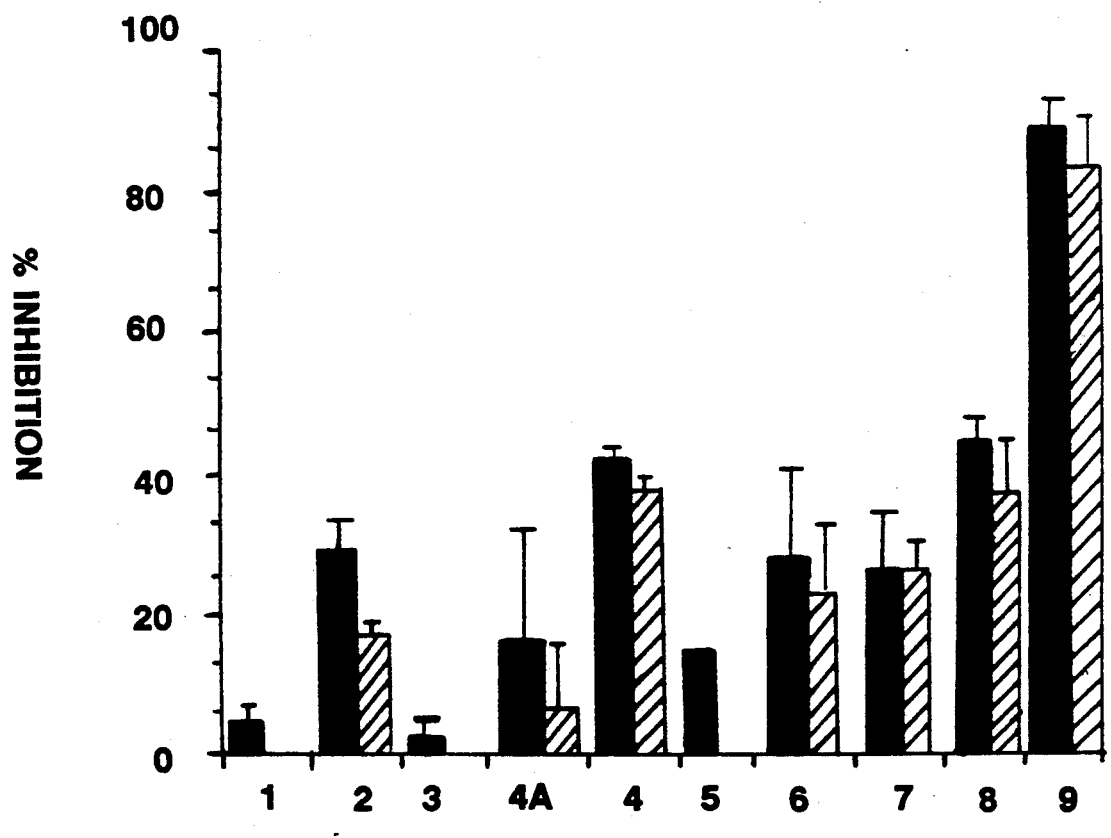
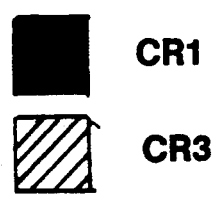

FIGURE 5
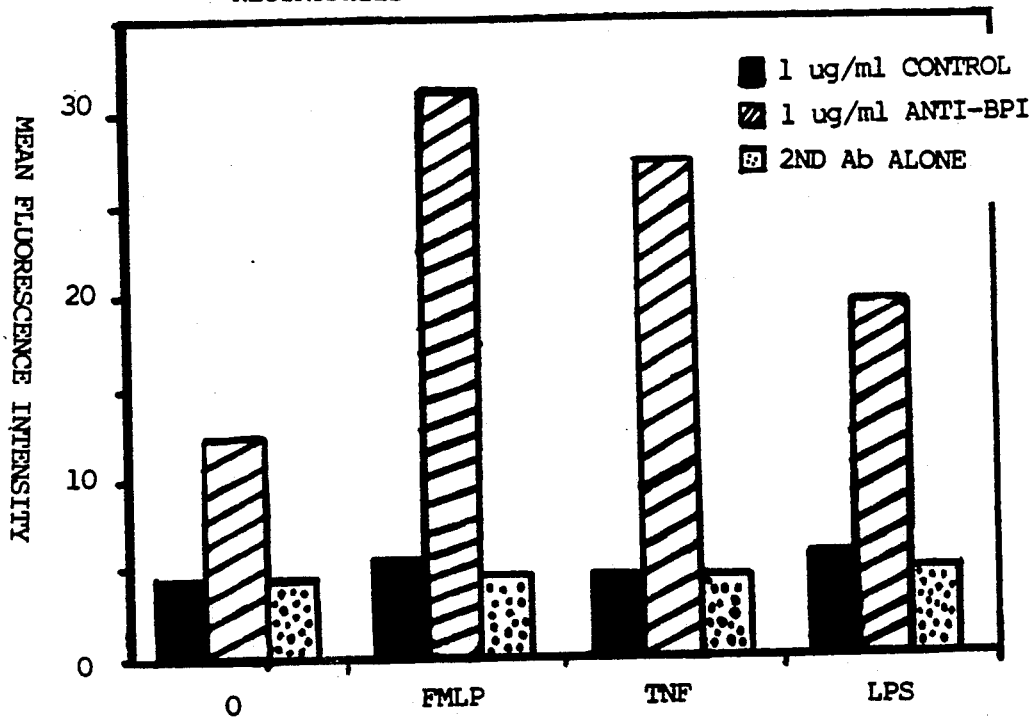
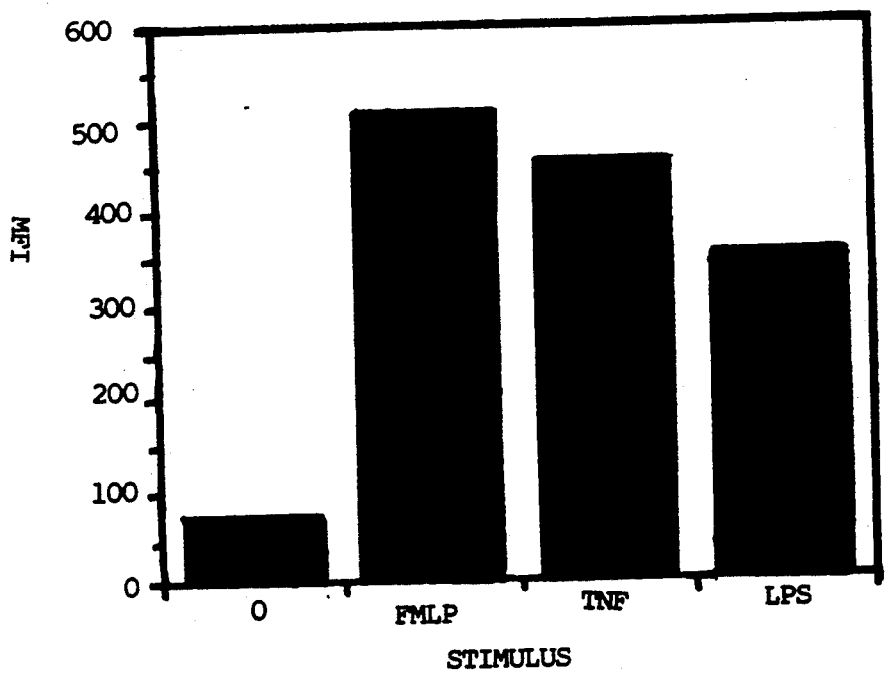

13/20

USE OF BACTERICIDAL/PERMEABILITY INCREASING PROTEIN OR BIOLOGICALLY ACTIVE ANALOGS THEREOF TO TREAT ENDOTOXIN-RELATED DISORDERS

This application is a continuation-in-part of U.S. Ser. No. 310,842 filed Feb. 14, 1989, now abandoned, the contents of which are hereby incorporated by reference.

BACKGROUND OF THE INVENTION

Gram negative infections are a major cause of morbidity and mortality especially in hospitalized and immunocompromised patients. [Duma, R. J., Am. J. of Med., 78 (Suppl. 6A): 154-164 (1985); and Kreger B. E., D. E. Craven and W. R. McCabe, Am. J. Med., 68: 344-355 (1980)]

Although available antibiotics are effective in containing the infection, they do nothing to neutralize the pathophysical effects associated with lipopolysaccharide (LPS). LPS, or endotoxin, is a major component of the outer membrane of gram negative bacteria and is releasaed when the organisms are lysed. [Ahenep, J. L. and K. A. Morgan, J. Infect. Dis., 150 (3): 380-388 (1984)]

LPS released during antibiotic therapy is a potent stimulator of the inflammatory response. Many detrimental effects of LPS in vivo result from soluble mediators released by inflammatory cells. [Morrison D. C. and R. J. Ulevich, Am. J. Pathol., 93 (2): 527-617 (1978)] LPS induces the release of mediators by host inflammatory cells which may ultimately result in disseminated intravascular coagulation (DIC), adult respiratory distress syndrome (ARDS), renal failure, and irreversible shock.

Monocytes and neutrophilic granulocytes play a key role in host defense against bacterial infections and also participate in the pathology of endotoxemia. These cells ingest and kill microorganisms intracellularly and also respond to LPS in vivo and in vitro by releasing soluble proteins with microbicidal, proteolytic, opsonic, pyrogenic, complement activating and tissue damaging effects. Tumor necrosis factor (TNF), a cytokine released by LPS stimulated monocytes mimics some of the toxic effects of LPS in vivo. Injecting animals with TNF causes fever, shock and alterations in glucose metabolism. TNF is also a potent stimulator of neutrophils.

Soluble LPS causes decreased neutrophil chemotaxis, increased adhesiveness, elevated hexose monophosphate shunt activity and $O_2$ radical production, upregulation of surface receptors for complement, and release of granule proteins into the surrounding medium. [Morrison and Ulevich (1978)]

Both specific and azurophil compartments degranulate in response to LPS. [Bannatyne, R. M., N. M. Harnett, K. Y. Lee and W. D. Rigger, J. Infect. Dis., 156 (4): 469-474 (1977)] Azurophil proteins released in response to LPS may be both harmful and beneficial to the host. Neutrophil elastase causes degradation of protease inhibitors responsible for suppressing the coagulation cascade. This results in coagulopathies such as disseminated intravascular coagulation, a potentially lethal consequence of endotoxemia. Azurophil granules also contain bactericidal molecules such as myeloperoxidase and BPI.

Rabbit BPI was first discovered in 1975. [Weiss, J., R. C. Franson, S. Becherdite, K. Schmeidler, and P. Elsbach, J. Clin. Invest., 55:33 (1975)] BPI was isolated from human neutrophils in 1978. [Weiss, J., P. Elsbach, I. Olson and H. Odeberg, J. Biol. Chem, 253 (8): 2664-2672 (1978)].

In 1989 a 57 kD protein with similar properties was isolated from human neutrophils. [Shafer, W. M., C. E. Martin and J. K. Spitznagel, Infect. Immun., 45:29 (1984)] This protein is identical to BPI by N-Terminal sequence amino acid composition, molecular weight and source. Although, the authors were unable to reproduce the chromatographic isolation procedure used by Elsbach, et al. and Weiss, et al.

Human BPI is a 57 kD protein which binds to the outer membrane of susceptible gram negative bacteria. [Weiss, et al. (1978)] The fact that BPI is a Lipid A binding protein is evidenced by: (1) rough strains of bacteria are more sensitive to both bactericidal and permeability increasing activities of BPI [Weiss, J., M. Hutzler and L. Kao, Infect. Immun., 51:594 (1986)]; (2) mutations in Lipid A caused decreased binding and increase resistance to bactericidal activity of both polymyxin B and BPI [Farley, M. M., W. M. Shafer and J. K. Spitznagel, Infect. Immun., 56:1589 (1988)]; (3) BPI competes with polymyxin B for binding to *S. typhimurium* [Farley 1988]; (4) BPI has sequence homology and immunocrossreactivity to another LPS binding protein Lipopolysaccharide Binding Protein (LBP). LBP-LPS complexes have been shown to stimulate the oxidative burst on neutrophils in response to formulated peptides. High density lipoprotein (HDL), another LPS binding protein, found in human serum in complex with LPS does not show the stimulatory effect on neutrophils. BPI binding disrupts LPS structure, alters microbial permeability to small hydrophobic molecules and causes cell death (Weiss, et al., 1978). BPI kills bacteria under physiologic conditions of pH and ionic strength in vitro indicating that it may be active in vivo outside the low pH environment of the phagolysosome. All of the bactericidal and permeability increasing activities of BPI are present in the N-terminal 25 kD fragment of the protein. [Ooi, C. E., J. Weiss, P. Elsbach, B. Frangione, and B. Marrion, J. Biol. Chem., 262: 14891 (1987)] Prior to the subject invention, however, it has been understood that the beneficial effects of BPI are limited to its bactericidal effects.

Despite improvements in antibiotic therapy, morbidity and mortality associated with endotoxemia remains high. Antibiotics alone are not effective in neutralizing the toxic effects of LPS. Therefore, the need arises for an adjunct therapy with direct LPS neutralizing activity. Current methods for treatment of endotoxemia use antibiotics and supportive care. Most available adjunct therapies treat symptoms of endotoxic shock such as low blood pressure and fever but do not inactivate endotoxin. Other therapies inhibit inflammatory host responses to LPS. As indicated below, present therapies have major limitations due to toxicity, immunogenicity, or irreproducible efficacy between animal models and human trials.

Polymyxin B is a basic polypeptide antibiotic which has been shown to bind to, and structurally disrupt, the most toxic and biologically active component of endotoxin, Lipid A. Polymyxin B has been shown to inhibit LPS activation of neutrophil granule release in vitro and is an effective treatment for gram negative sepsis in humans. However, because of its systemic toxicity, this drug has limited use except as a topical agent.

Combination therapy using antibiotics and high doses of methylprednisolone sodium succinate (MPSS) has been shown to prevent death in an experimental model of gram negative sepsis using dogs. Another study using MPSS with antibiotics in a multicenter, double blind, placebo-controlled, clinical study in 223 patients with clinical signs of systemic sepsis concluded that mortality was not significantly different between the treatment and placebo groups. Further, the investigators found that resolution of secondary infection within 14 days was significantly higher in the placebo group.

A relatively new approach to treatment of endotoxemia is passive immunization with endotoxin neutralizing antibodies. Hyperimmune human immunoglobulin against E. coli J5 has been shown to reduce mortality in patients with gram negative bacteremia and shock by 50%. Other groups have shown promising results in animal models using mouse, chimeric, and human monoclonal antibodies. Although monoclonal antibodies have advantages over hyperimmune sera, e.g. more consistent drug potency and decreased transmission of human pathogens, there are still many problems associated with administering immunoglobulin to neutralize LPS. Host responses to the immunoglobulins themselves can result in hypersensitivity. Tissue damage following complement activation and deposition of immune complexes is another concern in the use of therapies involving anti-endotoxin antibodies in septic patients. Also, immunoglobulins are large molecules, especially the pentameric IgMs currently in clinical trials, and are rapidly cleared by the reticuloendothelial system, diminishing the half-life of the drug.

Endotoxins elicit responses which are beneficial as well as damaging to the host. Endotoxemia induces production of LPS binding proteins from the liver and causes release of microbicidal proteins from leukocytes. In applicants' studies of neutrophil proteins involved in host defense, it has been determined that one of these proteins, BPI, is not only a potent microbicidal agent in vitro, but it also interferes with the ability of LPS to stimulate neutrophils. Specifically, it has been demonstrated that BPI binds to solve LPS and neutralizes its ability to activate neutrophils. Accordingly, this invention provides a therapeutic method for the treatment of LPS toxicity in gram negative septicemia.

SUMMARY OF THE INVENTION

The present invention provides a method of inhibiting lipopolysaccharide (LPS)-mediated stimulation of cells. This method comprises contacting the cells, in the presence of a cell-stimulating amount of lipopolysaccharide, with Bactericidal/Permeability Increasing Protein in an amount effective to inhibit cell stimulation.

The present invention additionally provides a method of treating a subject suffering from endotoxin-related shock caused by a gram negative bacterial infection which comprises administering to the subject an amount of BPI effective to treat the subject so as to alleviate the endotoxin-related shock.

Further, the invention provides a method of treating a subject suffering from disorder involving disseminated intravascular coagulation. The method comprises administering to the subject an amount of Bactericidal/Permeability Increasing Protein effective to alleviate the symptoms of disseminated intravascular coagulation and thereby treat the subject.

Further, the present invention provides a method of treating a subject suffering from endotoxemia caused by a gram negative infection which comprises administering to the subject an amount of Bactericidal/Permeability Increasing Protein effective to treat the subject suffering from endotoxemia.

As used herein endotoxemia means a condition in which the blood contains poisonous products, either those produced by the body cells or those resulting from microorganisms, i.e. gram negative bacteria.

The invention also provides a method of treating a subject suffering from endotoxin-related anemia caused by a gram negative bacterial infection which comprises administering to the subject an amount of Bactericidal/Permeability Increasing Protein effective to related anemia.

The present invention further provides a method of treating a subject suffering from endotoxin-related leukopenia caused by a gram negative bacterial infection. The method comprises administering to the subject an amount of Bactericidal/Permeability Increasing Protein effective to treat the subject so as to alleviate endotoxin-related leukopenia. Further, the invention includes a method of treating a subject suffering from endotoxin-related thrombocytopenia caused by a gram negative bacterial infection which comprises administering to the subject an amount of Bactericidal/Permeability Increasing Protein effective to treat the subject so as to alleviate endotoxin-related thrombocytopenia.

The invention also provides a method of inhibiting a pyrogen which comprises contacting the pyrogen with an amount of Bactericidal/Permeability Increasing Protein so as to inhibit the pyrogen.

Furthermore, the invention also includes a method of inhibiting lipopolysaccharide-mediated tumor necrosis factor production by cells which comprises contacting the cells in the presence of a cell-stimulating amount of lipopolysaccharide, with Bactericidal/Permeability Increasing Protein in an amount effective to inhibit lipopolysaccharide-mediated tumor necrosis factor production by cells.

The invention also includes a method of inhibiting gram negative bacteria-mediated tumor necrosis factor production by cells which comprises contacting the gram negative bacteria with Bactericidal/Permeability Increasing Protein in an amount effective to inhibit gram negative-mediated tumor necrosis factor production by cells.

Moreover, the invention includes a composition for the treatment of a subject suffering from endotoxin-related shock. The composition comprises a purified BPI or a biologically active polypeptide analog thereof in an amount effective to treat a subject suffering from endotoxin-related shock and a suitable carrier.

Further, the invention includes a composition for the treatment of a subject suffering from disseminated intravascular coagulation. The composition comprises a purified BPI or a biologically active polypeptide analog thereof in an amount effective to treat a subject from disseminated intravascular coagulation and a suitable carrier.

The invention also includes a composition for the treatment of a subject suffering from endotoxemia comprising a purified BPI or a biologically active polypeptide analog thereof in an amount effective to treat a subject suffering from endotoxemia and a suitable carrier.

The invention additionally provides a composition for the treatment of a subject suffering from endotoxin-related anemia comprising purified BPI or a biologically active polypeptide analog thereof in an amount effective to treat a subject suffering from endotoxin-related anemia and a suitable carrier.

Additionally, the invention provides a composition for the treatment of a subject suffering from endotoxin-related leukopenia. The composition comprises purified BPI or a biologically active polypeptide analog thereof in an amount effective to treat a subject suffering from endotoxin-related leukopenia and a suitable carrier. Further provided is a composition for the treatment of a subject suffering from endotoxin-related thrombocytopenia. The composition comprises purified BPI or a biologically active polypeptide analog thereof in an amount effective to treat a subject suffering from endotoxin-related thrombocytopenia and a suitable carrier.

As used herein endotoxin-related leukopenia is a condition, the manifestation of which is a decrease below the normal number of leukocytes in the peripheral blood. Moreover, as used herein endotoxin-related thrombocytopenia is a condition, the manifestation of which is a decrease below the normal number of thrombocytes.

Also, the invention provides a composition for inhibiting lipopolysaccharide-mediated tumor necrosis factor production by cells comprising purified BPI or a biologically active polypeptide analog thereof in an amount effective to inhibit lipopolysaccharide-mediated tumor necrosis factor production by cells and a suitable carrier. Moreover, the invention provides a composition for inhibiting tumor necrosis factor production by cells comprising purified BPI or a biologically active polypeptide analog thereof in an amount effective to inhibit gram negative bacteria-mediated tumor necrosis factor production by cells and a suitable carrier.

The invention provides a composition for inhibiting a pyrogen. The composition comprises purified BPI or a biologically active polypeptide analog thereof in an amount effective to inhibit a pyrogen.

Moreover, also provided is a method of preventing a disorder involving disseminated intravascular coagulation in a subject which comprises administering to the subject an amount of Bactericidal/Permeability Increasing Protein effective to prevent the symptoms of disseminated intravascular coagulation and thereby preventing the disorder.

Finally, the invention provides a method of isolating and recovering purified Bactericidal/Permeability Increasing Protein which comprises: (a) obtaining a crude sample of Bactericidal/Permeability Increasing Protein; and (b) separating the crude sample by column chromatography using de-pyrogenated solutions thereby isolating and recovering purified Bactericidal/Permeability Increasing Protein.

BRIEF DESCRIPTION OF THE FIGURES

FIG. 1a: Mean fluorescence intensity of CR1 on freshly isolated neutrophils was measured by FACS analysis. Cells were stimulated with varying doses of *E. Coli* 0111:B4 LPS as described in Materials and Methods. Since mean fluorescence intensity varies between individuals, the data is expressed as percent of the maximum response observed. Data shown represents the mean +/− Standard Error of three experiments.

FIG. 1b: 0111:B4 LPS (10 ng/ml) was preincubated with varying doses of crude azurophil extract for 30 minutes at 37° C. prior to testing for neutrophil stimulation. Data shown represents the mean +/− Standard Error of duplicates from a representative experiment. Values are expressed as % inhibition of the response to LPS alone.

FIG. 2: Crude azurophil extract was separated by reverse phase HPLC. Each peak was collected manually and protein concentrations were determined by amino acid analysis. An aliquot (1 μg) each of peak was dried in the presence of low endotoxin BSA, then redried in the presence of pyrogen free 0.1% acetic acid. Data shown represent the mean +/− Standard Error of duplicates from a representative experiment.

FIG. 5: (a) A bar graph illustrating BPI expression on the surface of neutrophils stimulated with FMLP, TNF, and LPS. (b) A bar graph illustrating maximal CR3 upregulation of human neutrophil cell surface expression.

DETAILED DESCRIPTION OF THE INVENTION

Figure 3A:
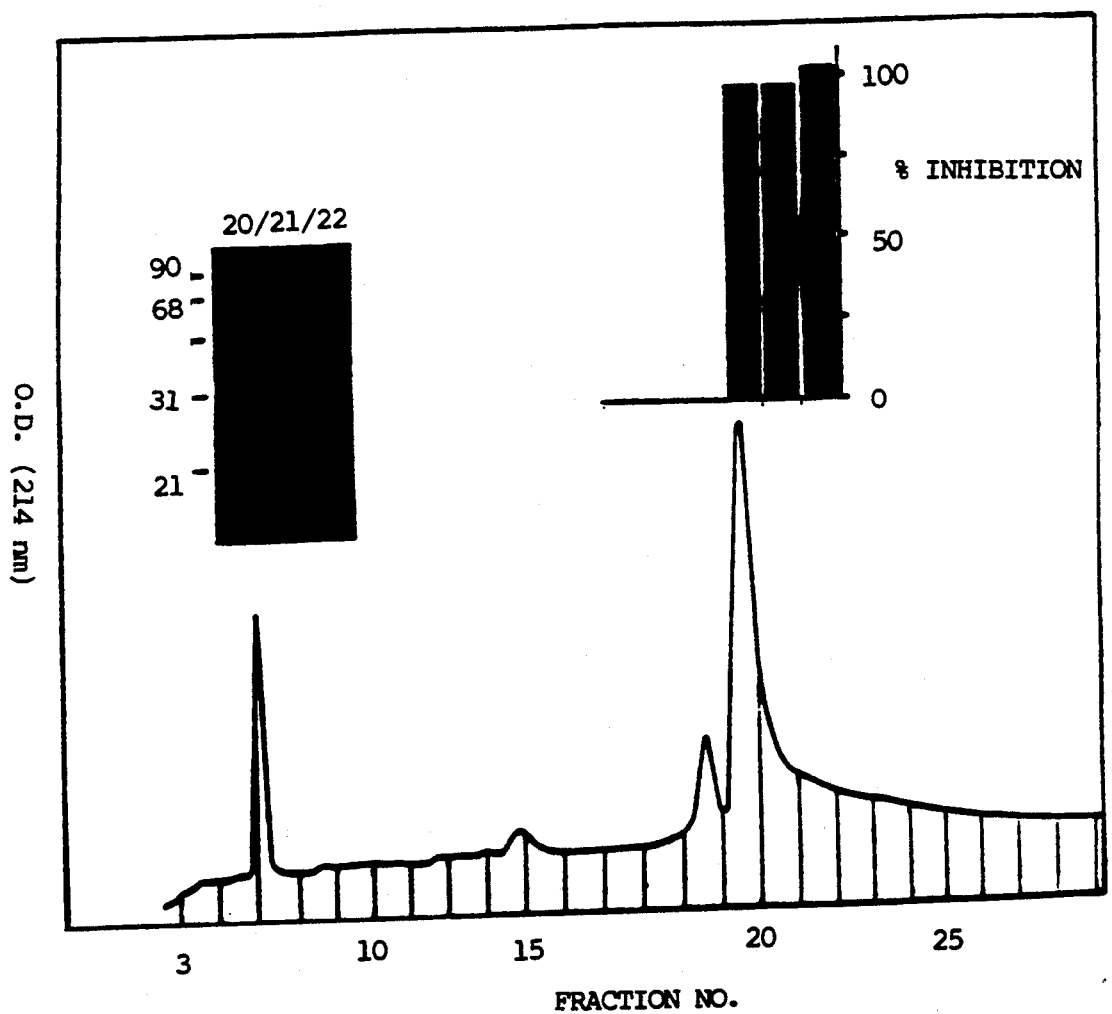
FIG. 3a: BPI purified by size exclusion followed by cation exchange HPLC was subjected to reverse phase HPLC and fractions were tested for LPS inhibitory activity.

The present invention provides a method of inhibiting lipopolysaccharide (LPS)-mediated stimulation of cells. This method comprises contacting the cells, in the presence of a cell-stimulating amount of lipopolysaccharide, with Bactericidal/Permeability Increasing Protein in an amount effective to inhibit cell stimulation.

The amount of Bactericidal/Permeability Increasing Protein effective to inhibit cell stimulation will vary according to the conditions present. The amount effective to inhibit cell stimulation is preferably from about 100 ng to about 100 mg, with the most preferred amount being from about 10 µg to about 10 mg.

Neutrophils and moncytes are the cells of greatest importance with regard to the application of the subject invention. However, other cells such as endothelial cells are also affected by LPS and may be used in this invention.

As used herein, human BPI or BPI means a naturally-occurring 57 kD protein which binds to the outer membrane of susceptible gram negative bacteria.

As used herein, Bactericidal/Permeability Increasing protein means 1) BPI, 2) any biologically active polypeptide which has substantially the same amino acid sequence as, and the biological activity of, BPI and 3) a biologically active fragment of BPI or polypeptide analogs of BPI. In this respect biologically active means capable of inhibiting the pyrogenic response to LPS. This biological activity is measured in the rabbit USP pyrogen assay.

In the preferred embodiment purified Bactericidal/Permeability Increasing Protein used used. Bactericidal/Permeability Increasing Protein also comprises recombinant Bactericidal/Permeability Increasing Protein and biologically active polypeptide analogs thereof. One suitable analog of Bactericidal/Permeability Increasing Protein comprises a polypeptide which has a molecular weight of about 25 kD and corresponds to the N-terminal amino acid sequence of Bactericidal/Permeability Increasing Protein.

As used herein a biologically active polypeptide analog of Bactericidal/Permeability Increasing Protein means a polypeptide which has substantially the same amino acid sequence as, and the biological activity of, native or naturally-occurring Bactericidal/Permeability Increasing Protein.

In the preferred embodiment the Bactericidal/Permeability Increasing Protein is administered in a pharmaceutically acceptable carrier. Pharmaceutically acceptable carrier encompasses any of the standard pharmaceutical carriers such as sterile solution, tablets, coated tablets and capsules. Typically such carriers contain excipients such as starch, milk, sugar, certain types of clay, gelatin, stensic acid, talc, vegetable fats or oils, gums, glycols, or other known excipients. Such carriers may also include flavor and color additives and other ingredients.

Compositions comprising such carriers are formulated by well known conventional methods. However, the composition comprising Bactericidal/Permeability Increasing Protein in an amount effective to suppress LPS mediated stimulation of neutrophils or monocytes is previously unknown.

In this method, the administration of the composition may be effected by any of the well known methods, including but not limited to, oral, intravenous, intramuscular, and subcutaneous administration.

In the practice of the method of this invention the amount of Bactericidal/Permeability Increasing Protein incorporated in the composition may vary widely. Methods for determining the precise amount are well known to those skilled in the art and depend inter alia upon the subject being treated, the specific pharmaceutical carrier and route of administration being employed, and the frequency with which the composition is to be administered.

The present invention additionally provides a method of treating a subject suffering from endotoxin-related shock caused by a gram negative bacterial infection which comprises administering to the subject an amount of Bactericidal/Permeability Increasing Protein treat the subject so as to alleviate the endotoxin-related shock. Endotoxins, as used herein, are substances containing lipopolysaccharide complexes found in the cell walls of microorganisms, principally gram-negative bacteria.

Further, the invention provides a method of treating a subject suffering from disorder involving disseminated intravascular coagulation. The method comprises administering to the subject an amount of Bactericidal/Permeability Increasing Protein effective to alleviate the symptoms of disseminated intravascular coagulation and thereby treat the subject.

As used herein, the term dissseminated intravascular coagulation is a complex disorder of the clotting mechanisms, in which coagulation factors are consumed at an accelerated rate, with generalized fibrin deposition and thrombosis, hemorrhages, and further depletion of the coagulation factors. Moreover, disseminated intravascular coagulation may be acute or chronic.

Further, the present invention provides a method of treating a subject suffering from endotoxemia which comprises administering to the subject an amount of Bactericidal/Permeability Increasing Protein effective to treat the subject suffering from endotoxemia.

As used herein endotoxemia means a condition in which the blood contains poisonous products, either those produced by the body cells or those resulting from microorganisms, i.e. gram negative bacteria.

The invention also provides a method of treating a subject suffering from endotoxin-related anemia which comprises administering to the subject an amount of Bactericidal/Permeability Increasing Protein effective to treat the subject so as to alleviate endotoxin-related anemia.

The present invention further provides a method of treating a subject suffering from endotoxin-related leukopenia. The method comprises administering to the subject an amount of Bactericidal/Permeability Increasing Protein effective to combat the gram negative bacterial infection and treat the subject so as to alleviate endotoxin-related leukopenia. Further, the invention includes a method of treating a subject suffering from endotoxin-related thrombocytopenia which comprises administering to the subject an amount of Bactericidal/Permeability Increasing Protein effective to treat the subject so as to alleviate endotoxin-related thrombocytopenia.

The invention also provides a method of inhibiting a pyrogen which comprises contacting the pyrogen with an amount of Bactericidal/Permeability Increasing Protein so as to inhibit the pyrogen. As used herein, a pyrogen is any fever-producing substance; exogenous pyrogens include bacterial endotoxins, especially of gram-negative bacteria; endogenous pyrogen is a thermolabile protein derived from such cells as polymor-phonuclear leukocytes which acts on the brain centers to produce fever.

Furthermore, the invention also includes a method of inhibiting lipopolysaccharide-mediated tumor necrosis factor production by cells which comprises contacting the cells in the presence of a cell-stimulating amount of lipopolysaccharide, with Bactericidal/Permeability Increasing Protein in an amount effective to inhibit lipopolysaccharide-mediate tumor necrosis factor production by cells.

The invention also includes a method of inhibiting gram negative bacteria-mediated tumor necrosis factor production by cells which comprises contacting the gram negative bacteria with Bactericidal/Permeability Increasing Protein in an amount effective to inhibit gram negative-mediated tumor necrosis factor production by cells.

The amount of Bactericidal/Permeability Increasing Protein effective to inhibit cell stimulation will vary according to the conditions present. The amount effective to inhibit cell stimulation is preferably from about 100 ng to about 100 mg, with the most preferred amount being from about 10 $\mu$g to about 10 mg.

In the above-described methods, the Bactericidal/Permeability Increasing Protein comprises recombinant Bactericidal/Permeability Increasing Protein. Moreover, Bactericidal/Permeability Increasing Protein a polypeptide which has a molecular weight of about 25 kD and corresponds to the N-terminal amino acid sequence of BPI.

Moreover, the invention includes a composition for the treatment of a subject suffering from endotoxin-related shock. The composition comprises a purified BPI or a biologically active polypeptide analog thereof in an amount effective to treat a subject suffering from endotoxin-related shock and a suitable carrier.

Further, the invention includes a composition for the treatment of a subject suffering from disseminated intravascular coagulation. The composition comprises a purified BPI or a biologically active polypeptide analog thereof in an amount effective to treat a subject suffering from disseminated intravascular coagulation and a suitable carrier.

The invention also includes a composition for the treatment of a subject suffering from endotoxemia comprising a purified BPI or a biologically active polypeptide analog thereof in an amount effective to treat a subject suffering from endotoxemia and a suitable carrier.

The invention additionally provides a composition for the treatment of a subject suffering from endotoxin-related anemia comprising purified BPI or a biologically active polypeptide analog thereof in an amount effective to treat a subject suffering from endotoxin-related anemia and a suitable carrier.

Additionally, the invention provides a composition for the treatment of a subject suffering from endotoxin-related leukopenia. The composition comprises purified BPI or a biologically active polypeptide analog thereof in an amount effective to treat a subject suffering from endotoxin-related leukopenia and a suitable carrier.

Further provided is a composition for the treatment of a subject suffering from endotoxin-related thrombocytopenia. The composition comprises purified BPI or a biologically active polypeptide analog thereof in an amount effective to treat a subject suffering from endotoxin-related thrombocytopenia and a suitable carrier.

Also, the invention provides a composition for inhibiting lipopolysaccharide-mediated tumor necrosis factor production by cells comprising purified BPI or a biologically active polypeptide analog thereof in an amount effective to inhibit lipopolysaccharide-mediated tumor necrosis factor production by cells and a suitable carrier. Moreover, the invention provides a composition for inhibiting tumor necrosis factor production by cells comprising purified BPI or a biologically active polypeptide analog thereof in an amount effective to inhibit tumor necrosis factor production by cells and a suitable carrier.

The invention provides a composition for inhibiting a pyrogen. The composition comprises purified BPI or a biologically active polypeptide analog thereof in an amount effective to inhibit a pyrogen.

Additionally, the invention provides a method of preventing a condition in a subject which comprises administering to the subject an amount of Bactericidal/Permeability Increasing Protein effective to prevent the condition. In the previously described method the condition is any of the conditions selected from the group consisting of endotoxin-related shock, endotoxemia, endotoxin-related anemia, endotoxin-related leukopenia, or endotoxin-related thrombocytopenia.

Moreover, also provided is a method of preventing a disorder involving disseminated intravascular coagulation in a subject which comprises administering to the subject an amount of Bactericidal/Permeability Increasing Protein effective to prevent the symptoms of disseminated intravascular coagulation and thereby preventing the disorder.

Finally, the invention provides a method of isolating and recovering purified Bactericidal/Permeability Increasing Protein which comprises: (a) obtaining a crude sample of Bactericidal/Permeability Increasing Protein; and (b) separating the crude sample by column chromatography using de-pyrogenated solutions thereby isolating and recovering purified Bactericidal/Permeability Increasing Protein. Moreover, in this method the Bactericidal/Permeability Increasing Protein comprises native Bactericidal/Permeability Increasing Protein or a biologically active polypeptide analog thereof. Further, a biologically active polypeptide analog of Bactericidal/Permeability Increasing Protein comprises a polypeptide which has a molecular weight of about 25 kD and corresponds to the N-terminal amino acid sequence of Bactericidal/Permeability Increasing Protein. We have found that biological activity level of Bactericidal/Permeability Increasing Protein varies depending on the method used for obtaining Bactericidal/Permeability Increasing Protein. It appears that depyrogenated Bactericidal/Permeability Increasing Protein, i.e. Bactericidal/Permeability Increasing Protein isolated and recovered by the above-described method using de-pyrogenated solutions, shows a much higher level of biological activity than pyrogenated Bactericidal/Permeability Increasing Protein (Table 6).

This invention is illustrated in the Experimental Details and Results sections which follow. These sections are set forth to aid in an understanding of the invention but are not intended to, and should not be construed to, limit in any way the invention as set forth in the claims which follow.

EXPERIMENTAL DETAILS

Example 1

Materials and Methods: Reagents

Lipopolysaccharide from *E. Coli* 0.111:B4, *S. typhimurium* wild type, glycolipid from *S. typhimurium* RE mutant, and Lipid A from *S. typhimurium* RE mutant, and LPS from *P. aeruginosa* were purchased from RIBI Immunochem Research, Inc., Hamilton, Mont.; Fmet-Leu-Phe (FMLP) and polymyxin B Sulfate from Sigma Chemical Co., St. Louis, Mo.; Hank's Balanced Salt Solution without calcium, magnesium and phenol red (HBSS) from Hazelton Research Products, Denver, Pa., Ficoll-Paque, Percoll and Macrodex from Pharmacia Inc., Piscataway, N.J.; TNF and anti-TNF from Endogen, Boston, Mass., Fluorescein conjugated goat-anti-mouse IgG from TAGO Inc., Burlingame, Calif.: IgG1 control antibody from Coulter Immunology, Hialeah, Fla.; Phycoerythrin (PE) conjugated anti CR3 (Leu-15) and IgG2a control from Becton Dickinson, Mountain View, Calif., Anti CR1 monoclonal antibody, Yz−1, was a kind gift from Dr. Rick Jack at Harvard University.

Azurophil Granule Isolation and Extraction

Granulocytes were isolated from buffy coats obtained from local blood banks. Buffy coats were diluted 3-4X in HBSS and granulocytes were separated from mononuclear cells by centrifugation through 64% Percoll. The pellet was subjected to diisopropylfluorophosphate (DFP), washed, and resuspended in ice cold lysis buffer (10 mM PIPES, pH 6.8, 100 mM KCL, 3 mM NaCl, 3.5 mM MgCl2) and disrupted by nitrogen cavitation (Parr Instrument Co., Moline, Ill.). Azurophil granules were isolated on discontinuous Percoll gradients as described by Borregaard. [Borregaard, N., J. M. Heiple, E. R. Simons, and R. A. Clark, J. Cell. Boil., 97: 52-61 (1983)] The azurophil granules were collected and Percoll was removed by centrifugation at 180,000×G for 2 hours. The granules were lysed by 4 cycles of freeze-thaw followed by 1 minute of sonication. The lysed granules were extracted in an equal volume of 100 mM glycine, pH 2 by vortexing intermittently for 1 hour at room temperature. The acid extract was clarified by centrifugation at 30,000×G for 20 minutes and at 200,000×G for 30 minutes.

Neutrophil Isolation

Venous blood was drawn from healthy volunteer donors into acid citrate dextrose anticoagulant and immediately placed on ice. Five parts of blood were mixed with 1 part of cold Macrodex, and allowed to settle for 1.5-2 hours at 4° C. Leukocyte-rich plasma was washed 1X in cold HBSS, then resuspended in HBSS and layered over Ficoll-Paque. If significant erythrocyte contamination was present, the granulocyte pellet was subjected to hypotonic lysis. The cells were washed 2× in HBSS and resuspended in HBSS+2% autologous plasma to give a final granulocyte concentration of $1 \times 10^6$/ml in the incubation mixture.

BPI Purification

Approximately 2 mg of crude azurophil granule extract was separated by size on a Biosil (TSK-250) (7.8 mm×600 mm) high performance size exclusion column using 50 mM glycine and 100 mM NaCl, pH 2.0, under isocratic conditions of a flow rate of 1 ml/min. Column fractions with the greatest LPS inhibitory activity contained a large proportion of the 54 KD species as shown by SDS PAGE. These TSK fractions were pooled and run over an Aquapore weak cation exchange (WCX) column (2.1 mm×30 mm) using 50 mM citrate, pH 5.5, and eluted in a gradient of 0-75%, of 50 mM citrate and 1M NaCl (Buffer B) in 25 min, then 75-100% Buffer B in 5 min with a flow rate of 200 ml/min. Material of 57 KD was recovered from cation exchange and appeared as a single band on SDS page. In some experiments BPI was further purified by reverse phase HPLC on a Vydac C4 column loaded for 12 min in 0.1% $CH_3CN$ plus 0.1% TFA, in 30 min with a flow rate of 200 ml/min (Raining Instruments, Emergyville, Calif.).

Neutrophil Stimulation

Isolated neutrophils were kept on ice until incubated with and without stimuli at 37° C. for 30 minutes. Following the incubation, cells were washed in a large volume of cold PBS+0.05% Na Azide+2% autologous plasma. Pellets were divided in two, one stained with 50 μl control IgG1 antibody (20 μg/1×10⁶ cells), the other with 50 μl of 20 lg/1×10⁶ cells anti-CR1 for 30 minutes at 0° C. Following this incubation the cells were washed 2× with PBS+autologous plasma, then stained with goat-anti-mouse IgG-FITC, and in some experiments, 20 μl of IgG2a-phycoerythrin (PE) in control wells, and 20 μl Leu-15 PE in test wells. Following a 30 minute incubation at 0° C. and 2 more washes, the cells were analyzed by flow cytometry on a Becton Dickinson FACStar flow cytometer (Becton Dickinson, Mountain View, Calif.). Neutrophil stimulation was measured by comparing means fluorescence intensity of samples which had been incubated in HBSS+2% autologous plasma alone (control) to those incubated with LPS or LPS which had been preincubated for 30 minutes at 37° C. with BPI or polymyxin B. Data are expressed as % stimulation or % inhibition and were calculated using the mean fluorescence intensity (Fl), on a log scale, according to:

% Stimulation=[(Experimental−Control)/(Maximum−control)]×100 and

% Inhibition=1−[(+Inhibitor)−(Control)]/[(−Inhibitor)−(Control)]×100.

Amino Acid Analysis

Vapor phase hydrolysis of BPI and amino acid derivitization was performed using a Pico-tag Workstation (Waters, Milford Mass.) and chromatographic analysis of the phenylthiocarbamyl amino acids was performed on an applied Biosystems 130 A MPLC using Protocols provided by the manufacturer.

Sequence Analysis

BPI N-terminal sequence was anlayzed by automated Edman degradation using an applied Biosystems 477A pulse liquid phase sequenator (Applied Biosystems, Foster City, Calif.). Phenyltheohydantion amino acid analysis was performed on line using an applied biosystems Model 120A liquid chromatograph.

RESULTS

Human neutrophils may be stimulated both in vivo and in vitro by lipopolysaccharide. Upon activation, surface expression for C3b and C3bi (CR1 and CR3 respectively), increases. Using the Fluorescence Activated Cell Sorter (FACS), fluorescence intensity of freshly isolated human neutrophils was measured following stimulation with increasing doses of 0111:B4 LPS (FIG. 1a). Because commonly observed maximum stimulation as at or above 10 ng/ml, experiments testing for inhibition of 0111:B4 LPS using 10 ng/ml as the stimulatory dose. All experiments were performed in duplicate. In most experiments, data is shown only for CR1 since we did not observe any condition where neutrophil stimulation caused upregulation of CR1 or CR3 along (M. Marra et al. (1990) *J. Immunol.* 144(2):662–666).

To determine whether proteins found in neutrophil azurophil granules could interfere with the neutrophil response to LPS, crude acid extracts of azurophil granules were pre-incubated with LPS for 30 minutes at 37° C. The mixture was then tested for its ability to stimulate neutrophils. Azurophil protein (1 μg/ml) could effectively block stimulation of $1 \times 10^6$ polymorphonuclear leukocytes (PMN)/ml by 10 ng/ml of LPS (FIG. 1b). This effect was not observed using glycine extraction buffer preincubated with LPS, nor was there any stimulation of neutrophils using crude extract or glycine buffer control (data not shown).

To further investigate which of the proteins in the extract was/were responsible for inhibitory effect, crude acid extracts were separated by reverse phase HPLC; each peak was assayed separately for LPS inhibitory activity. The identity of each of the peaks was previously determined using a two-dimensional purification approach involving microbore reverse phase HPLC in first dimension followed by SDS PAGE, electroblotting and microsequencing. The azurophil proteins can be resolved into 10 discrete peaks whose identities are shown in Table 1. The amino acid sequences shown are for the last 15 amino acids of the N-terminal.

TABLE 1

AZUROPHIL GRANULE-DERIVED PROTEINS

| Peak | Identity | Sequence (1  5  10  15) |
|---|---|---|
| 1 | Defensins (HNP-2) | CYCRIPACIAGERRY |
| 2 | Granulocidin (HNP-4) | VCSCRLVFCRRTGLR |
| 3 | Eosinophil Cationic Protein (ECP) | XPPQFTRAQWFAIQH |
| 4a | Eosinophil-Derived Neurotoxin (EDN) | KPPQFTXAQXFETQX |
| 4b | Cathepsin G | IIGGRESRPHSRPYM |
| 5a | Lysozyme | KVFERXELARTLKRL |
| 5b | Eosinophil Major Protein (MBP) | TCRYLLVRSLQTFSQ |
| 6 | Unknown | IVGGRKARPXQFPFL |
| 7 | Unknown | IVGGHEAQPHSRPYM |
| 8a | Myeloperoxidase | VNCETSCVQQPPCFP |
| 8b | Elastase | IVGGRRARPHAXPFM |
| 9 | Bactericidal/Permeability Increasing Protein (BPI) | VNPGVVVRISQKGLD |

LPS inhibitory activity of 1 μg of each peak is shown in FIG. 2. As shown, peak 9 had the highest LPS neutralizing activity. The major protein species in this peak has N-terminal identity with Bactericidal/Permeability Increasing Protein (BPI) described previously (Weiss, J., P. Elsbach, I. Olsson and H. Odeberg, *J. Biol. Chem*, 253(8):2664–2672 (1978)). BPI has been shown to contain the majority of the gram negative bactericidal activity in azurophil granule protein extracts. Cathepsin G shows some inhibition of LPS, but the data between experiments were not as reproducible as for peak 9. Cathepsin G has been shown to bind to LPS in vitro and to kill gram negative organisms, although to a lesser extent than BPI. Other proteins which have demonstrated microbicidal activity against gram negative organisms are elastase and the defensins. However, these proteins (1 μg/ml) did not inhibit the stimulatory activity of LPS on neutrophils.

Figure 3B:
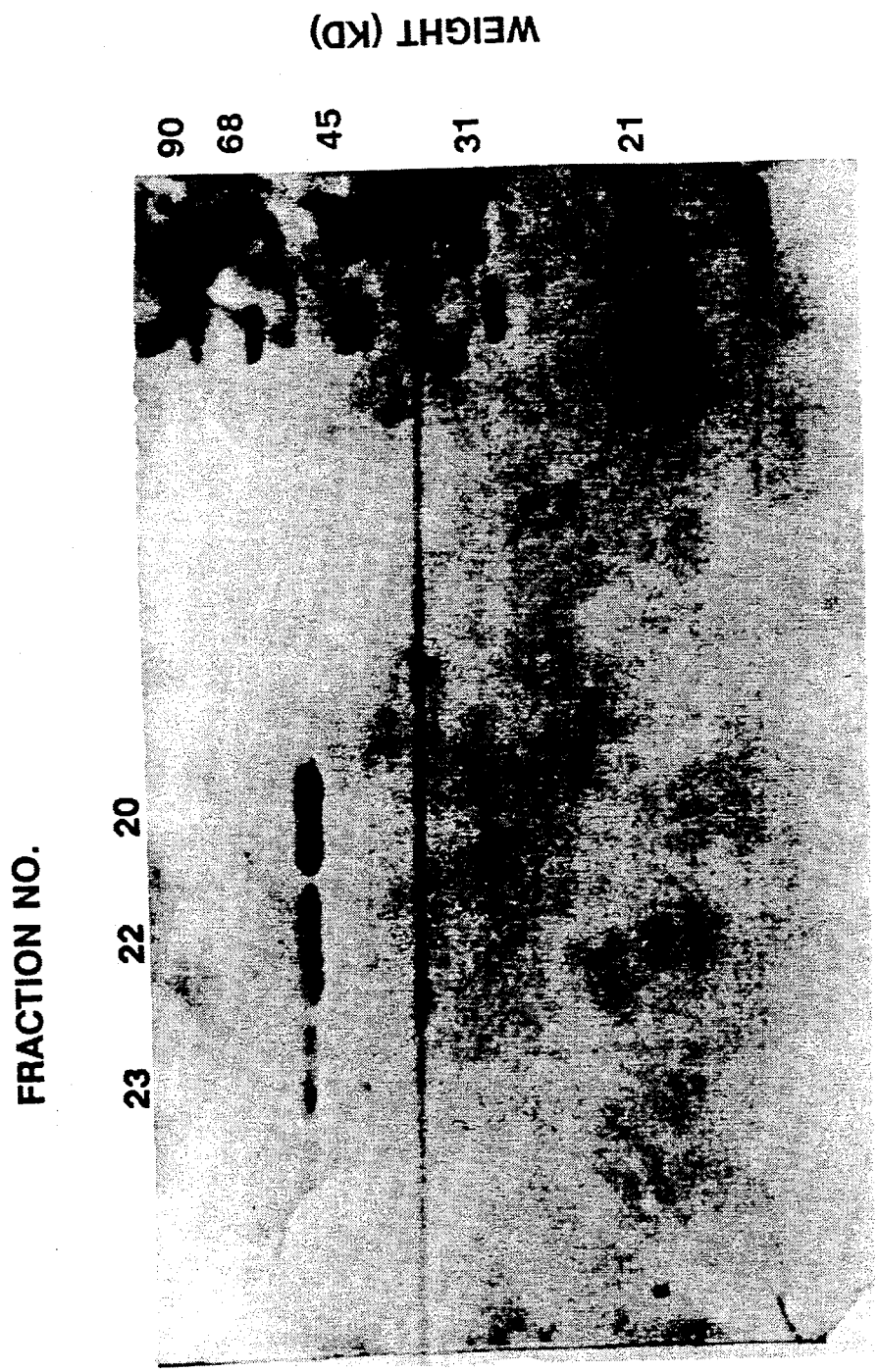
FIG. 3b: Data show the RPLC profile of the 2X purified material along with the inhibitory activity and SDS PAGE analysis of fractions 20,21 and 22.

LPS inhibitory activity of crude azurophil extracts was further characterized and purified using size exclusion and ion exchange followed by reverse phase chromatography. LPS inhibitory activity comigrates with a pure 57 KD band seen on SDS PAGE (FIG. 3b).

Figure 4A:
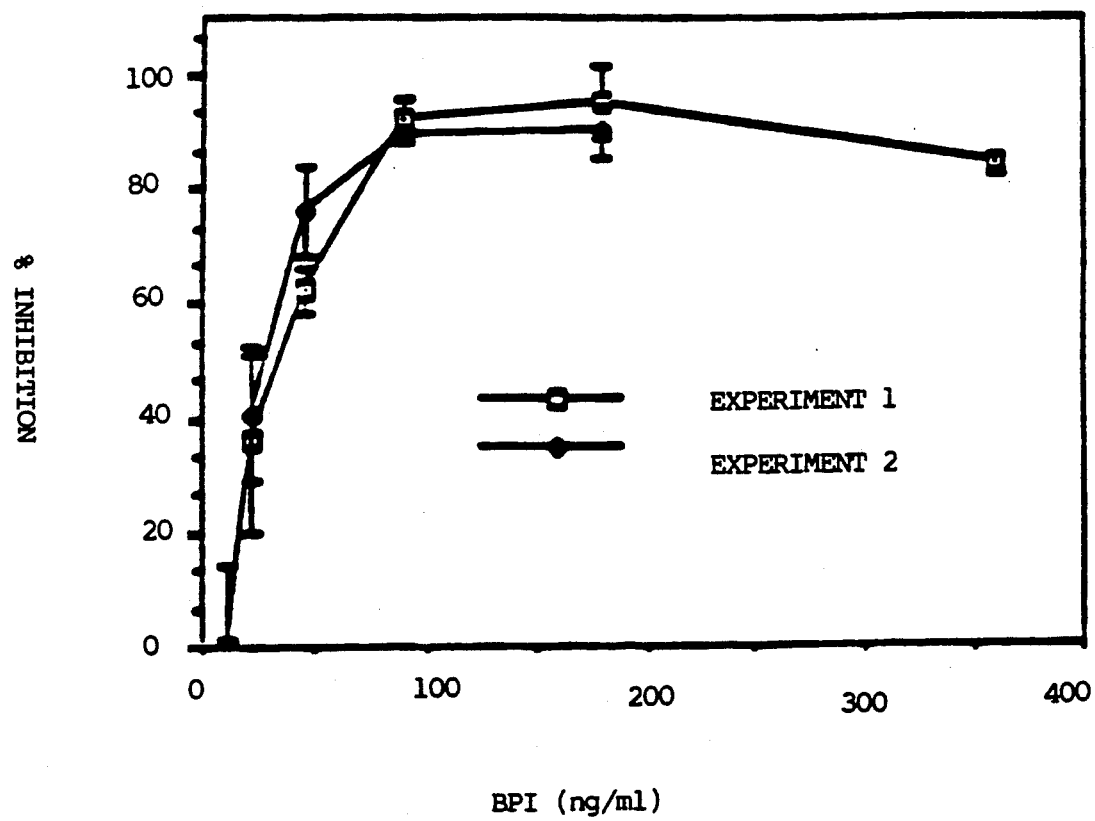
FIG. 4: 0111:B4 LPS (10 ng/ml) was preincubated with varying doses of (A) purified BPI, and (B) polymyxin B, then tested for neutrophil stimulatory activity. Results from two experiments show inhibition of complement receptor expression on neutrophils with Standard Errors for replicate samples.

Because the buffer used in the RPLC separations [CH$_3$CN and 0.1% trifluoroacetic acid (TFA)] significantly diminishes the LPS inhibitory activity of BPI (data not shown), and since the material purified from ion exchange chromatography was of high purity as judged by SDS PAGE, size exclusion/ion exchange material was used to generate a dose response curve (FIG. 4a). Data is shown from two experiments, each performed in duplicate. This size exclusion/ion exchange purified material was confirmed to be BPI by N-terminal sequence analysis. Protein concentration was determined by amino acid analysis.

As seen in FIG. 4a, about 90 ng/ml of BPI is required for maximal inhibition of the neutrophil response to 10 ng/ml 0111/B4 LPS. The neutrophil response to formulated peptide ($10^{-7}$M FMLP) was not inhibited by BPI (data not shown).

Figure 4B:
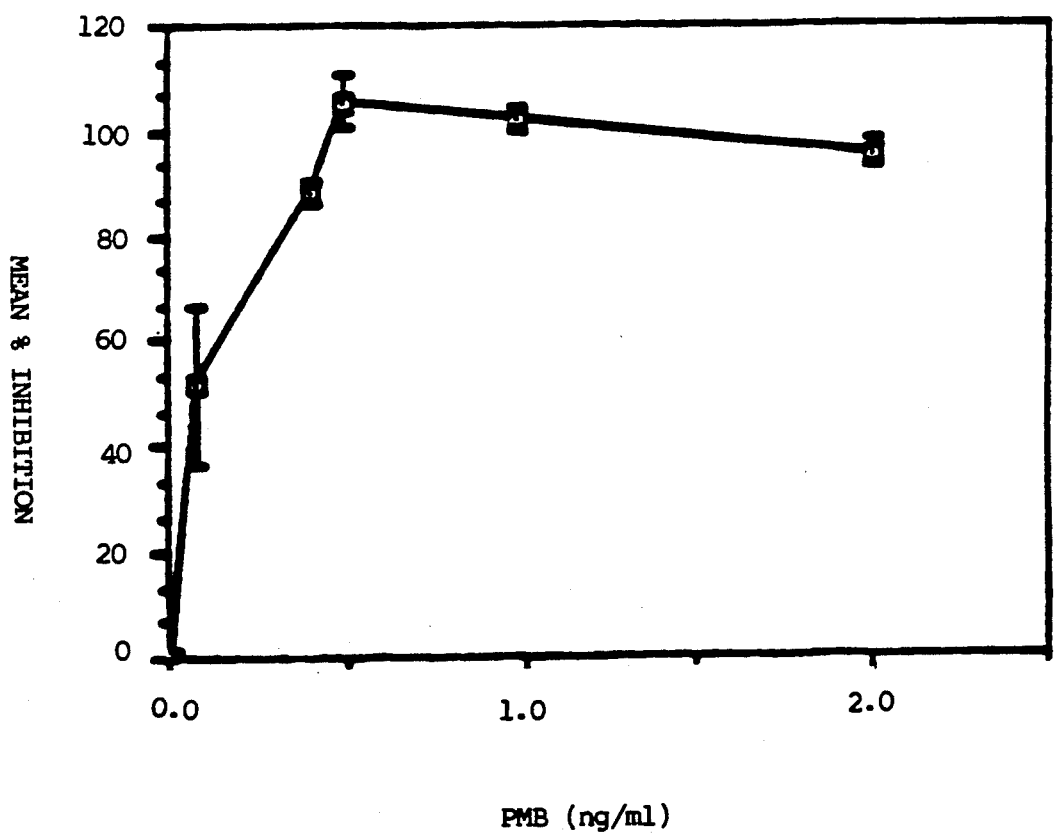

FIG. 4b shows a similar does response curve for the polypeptide antibiotic Polymyxin B (PMB). Polymyxin B binds to the Lipid A moiety of LPS and neutralizes some of its toxic effects both in vivo and in vitro. Polymyxin B has been demonstrated to bind to LPS stiochiometrically (Morrison, D. C. and D. M. Jacobs, Immunochem, 13: 813–818 (1976)). The calculated amount of PMB required to inhibit 10 ng/ml of smooth LPS is approximately 0.67 nM. In the subject experiments 0.4 ng/ml, or 0.36 nM of polymyxin B was required to completely inhibit neutrophil stimulation using 10 ng/ml of LPS. 90 ng/ml, or 1.58 nM BPI was required for 100% inhibition of 10 ng/ml LPS.

Therefore, on a molar basis the amount of BPI required to inhibit LPS stimulation of neutrophils in vitro was approximately 4X the amount required for polymyxin B.

To test whether BPI can inhibit LPS from other gram negative organisms, LPS molecules with varying polysaccharide chain lengths and Lipid A were tested in the subject system against 90 ng/ml of 2X purified BPI. data shown in Table 2 demonstrates that although the stimulatory dose may vary between these molecules, LPS from both smooth and rough chemotypes as well as Lipid a are all inhibited by BPI.

TABLE 2

| LPS | 10 NG/ML | 1 NG/ML |
|---|---|---|
| *E. COLI* 0111:B4 | 97 | * |
| *S. TYPHIMURIUM* WILD TYPE | 103 | 113 |
| *S. TYPHIMURIUM* RE MUTANT | 113 | 109 |

TABLE 2-continued

| | 10 NG/ML | 1 NG/ML |
|---|---|---|
| S. TYPHIMURIUM RE MUTANT LIPID A | 33 | 99 |
| P. AERUGINOSA | 112 | * |

*Low to no stimulation at this endotoxin concentration

Example 2

I. Preliminary Studies on Neutrophil BPI

As previously discussed, Bacterial/Permability-Increasing protein (BPI) is a cationic 50-60,000 m.w. protein first purified from human neutrophil granules by Weiss et al. (Weiss, J., P. Elsbach, I. Olsson and H. Odegerg. 1978. J. Biol. Chem. 253:2664). BPI alters bacterial cell membrane permeability and has bactericidal activity specifically against gram negative organisms. To date, the literature on BPI has focused exclusively on its bactericidal activity.

We report that BPI binds to LPS and inhibits both neutrophil and monocyte responses to soluble LPS in vitro. BPI also inhibits LPS activity in the Limulus Amebocyte Lysate assay. Our research has identified BPI as a lead molecule for the development of novel therapies against endotoxic shock.

In response to LPS, human neutrophils upregulate cell surface expression of complement receptors CR1 and CR3 (FIGS. 1a and 5b). To measure this neutrophil response to LPS, we incubated freshly isolated human neutrophils with E. Coli 0111:B4 LPS (FIG. 4a), and shows that maximal CR1 upregulation is observed using 10 ng/ml LPS (FIG. 4). Neutrophil stimulation with LPS was not inhibited by exogenous anti-TNF antibodies, suggesting that LPS acted directly on neutrophils in this system.

BPI inhibits the neutrophil response to LPS (FIG. 4a). Inhibition of CR upregulation was complete at a dose of approximately 1.8-3.6 nM (100-200 ng/ml) BPI compared to 0.4 nM polymyxin B required to inhibit 10 ng/ml smooth LPS (approximate m.w. 15,000) is about 0.7 nM, matching closely with the observed value of 0.4 nM. On a molar basis, the amount of BPI required to inhibit LPS was approximately 5-fold greater than the amount required for polymyxin B.

BPI inhibits LPS-mediated neutrophil stimulation but not stimulation by either FMLP or TNF (Table 3). These data demonstrate that BPI inhibits LPS directly and does not disrupt neutrophil mechanisms involves in CR upregulation.

Figure 6:
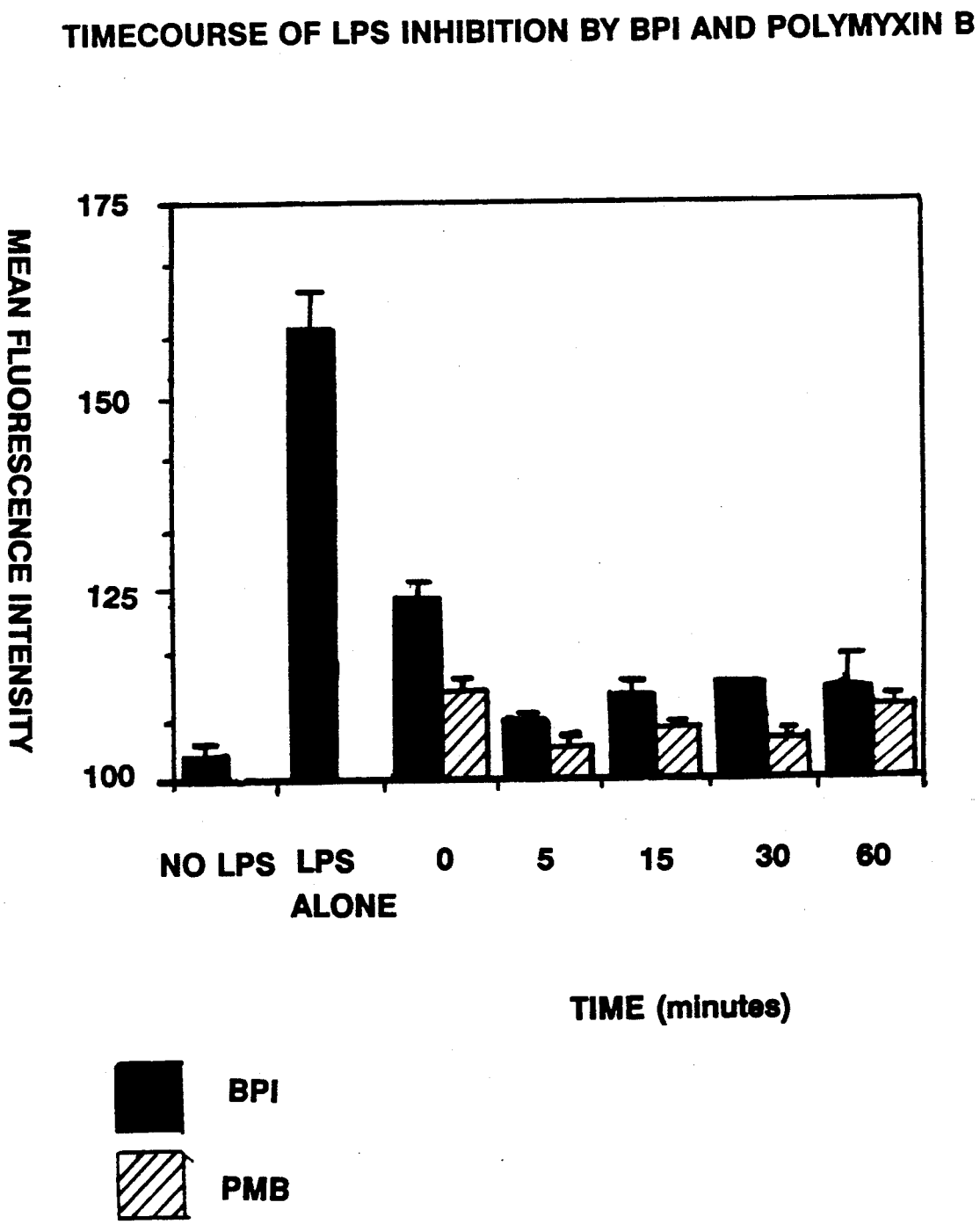
FIG. 6: A bar graph illustrating that BPI and polymyxin B inhibited more than 7% of the neutrophil response to LPS.

Neutralization of LPS by BPI occurred rapidly. Even without preincubation, both BPI (and polymyxin B) inhibited more than 7% of the neutrophil response to LPS (FIG. 6). Maximal inhibition was seen following only 5 minutes of preincubation.

BPI inhibits CR upregulation stimulated by LPS from smooth and rough bacterial strains, as well as lipid A (Table 4) Because of the board range of BPI activity against these different forms of LPS, among which only lipid A and 2-keto-3-deoxy-octanoate are shared determinants, it is likely that LPS inhibition by BPI is affected through lipid A.

Figure 7:
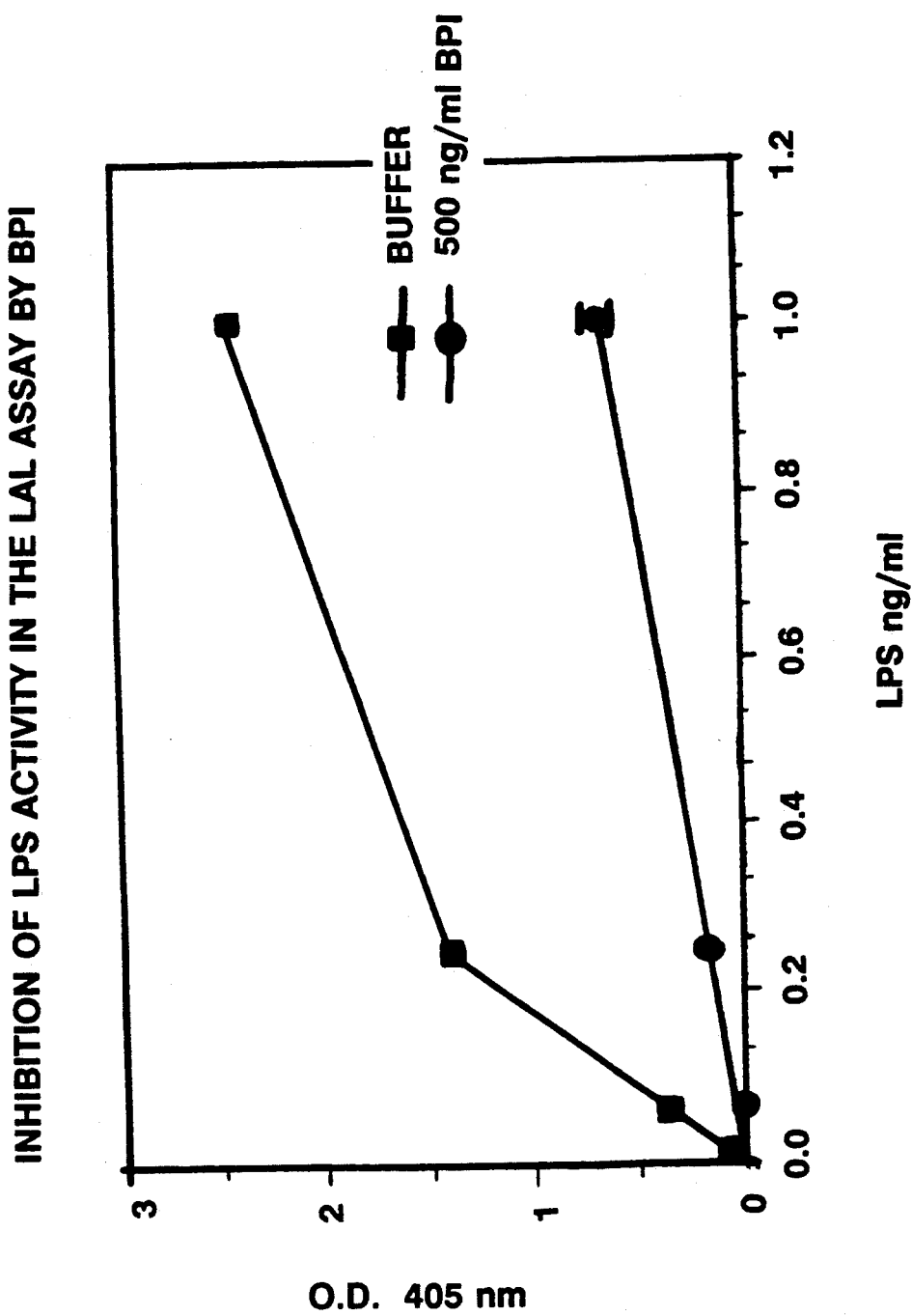
FIG. 7: A graph illustrating that BPI inhibits LPS activity.

BPI inhibits other LPS-mediated activities. At a concentration of approximately 9 nM, or 500 ng/ml, BPI significantly inhibited LPS activity in the LAL assay (FIG. 7). When LPS and BPI were added together without preincubation no inhibition was observed (data not shown), indicating that BPI acted on LPS, and had no effect on the LAL assay system. BPI also inhibits LPS-mediated TNF production by human adherent mononuclear cells (Table 5).

TABLE 3

Effect of BPI on Neutrophil Stimulation by Various Agents

Inhibition of CR Upregulation on Neutrophils

| Stimulus | Dose | % Inhibition CR1 | % Inhibition CR3 |
|---|---|---|---|
| LPS | 10 ng/ml | 109 | 102 |
| FMLP | $10^{-7}$ M | 9 | 11 |
| rTNF | 50 U/ml | 0 | 0 |

Neutrophils were incubated with E. Coli 0111:B4 LPS, FMLP or TNF preincubated in the presence or absence of 2.7 nM BPI. Data is reported as percent inhibition of CR expression in response to each stimulus preincubated with buffer alone.

TABLE 4

Inhibition of LPS and Lipid A induced Neutrophil Stimulation by BPI

Inhibition of CR Upregulation on Neutrophils

| Stimulus | Dose (ng/ml) | CR1 % Inhibition | CR3 % Inhibition |
|---|---|---|---|
| None | — | 0 | 0 |
| E. Coli 011:B4 LPS | 10 | 100 | 99 |
| S. typhimurium Wild Type LPS | 10 | 104 | 100 |
| S. typhimurium RE Mutant LPS | 1 | 97 | 95 |
| S. typhimurium RE Mutant Lipid A | 1 | 111 | 104 |

Neutrophils were stimulated with LPS and lipid A preincubated with and without 2.7 nM purified BPI. Results are expressed as percent inhibition of fluorescence intensity observed with each type of LPS alone.

TABLE 5

BPI Inhibits LPS-Induced TNF Production by Human Monocytes
TNF (pg/ml) Produced in Response to LPS Preincubated With*:

| LPS (ng/ml) | Medium Alone | 100 ng/ml Polymyxin B | 500 ng/ml BPI | 250 ng/ml BPI | Buffer Control |
|---|---|---|---|---|---|
| 0 | 0 | 0 | 0 | 0 | 0 |
| 0.1 | 61 | 0 | 0 | 0 | 81 |
| 1 | 1051 | 96 | 0 | 0 | 1090 |
| 10 | 2053 | 2154 | 1490 | 1746 | 2325 |

*E. Coli 0111:B4 LPS, was preincubated with BPI or polymyxin B (PMB), than added to adherent peripheral blood mononuclear cells. TNF production was assayed by ELISA.

BPI was first purified by Elsbach and Weiss in 1978. In our initial studies we isolated BPI from azurophil granule extracts in a single step by reverse phase HPLC. Recovery of BPI activity from reverse phase was poor, probably due to the denaturing conditions. Here we show the purification of LPS inhibitory activity using only non-denaturing steps and demonstrate that most of the activity from neutrophils comigrates with BPI. Improvements in the purification have also led to very high specific activity material as will be shown in the following section.

Figure 8:
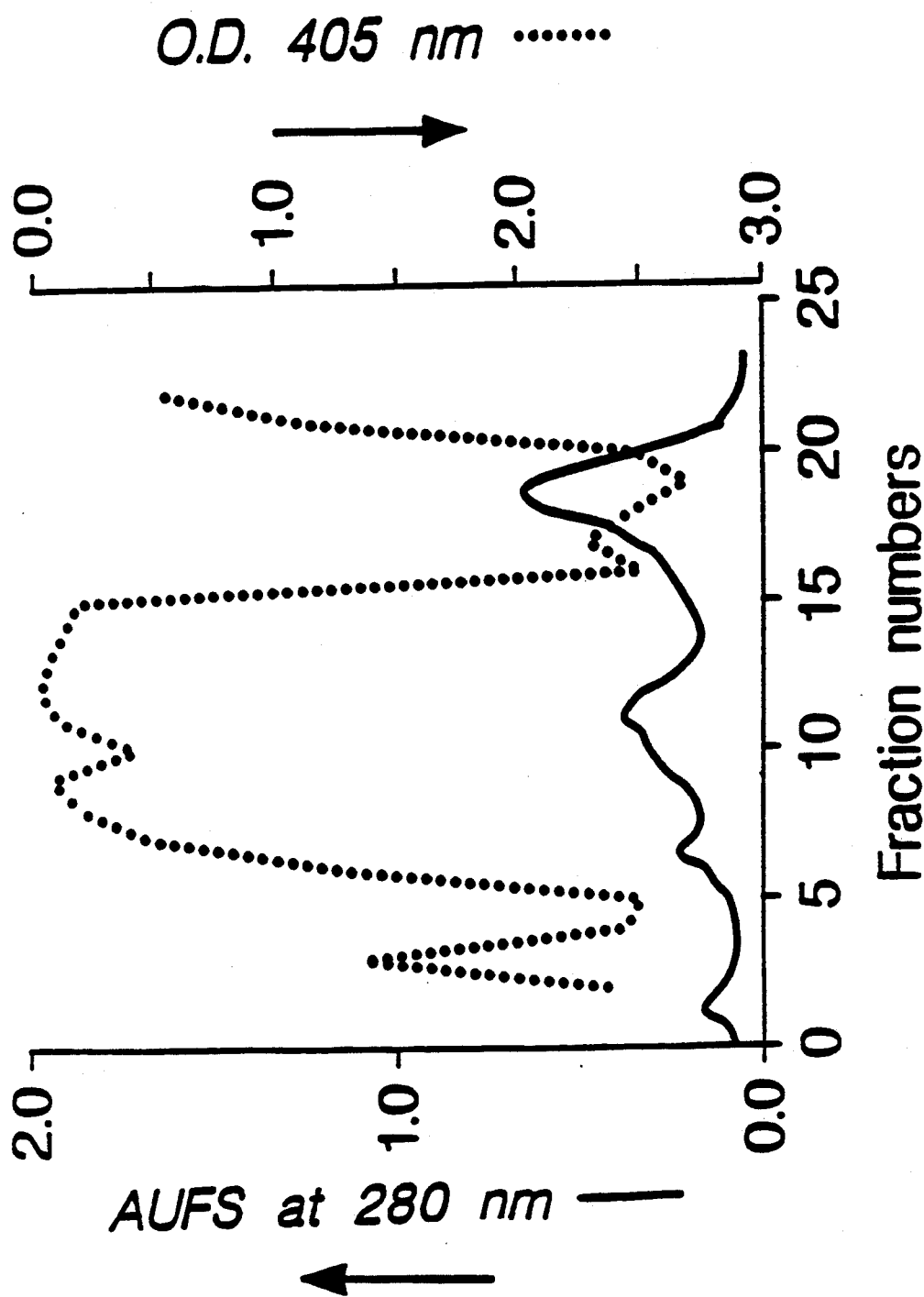
FIG. 8: A chromatogram showing a fractionated azurophile granule extract by cation exchange HPLC; the dotted line traces LPS inhibitory activity and the solid line traces protein absorbance.
Figure 9:
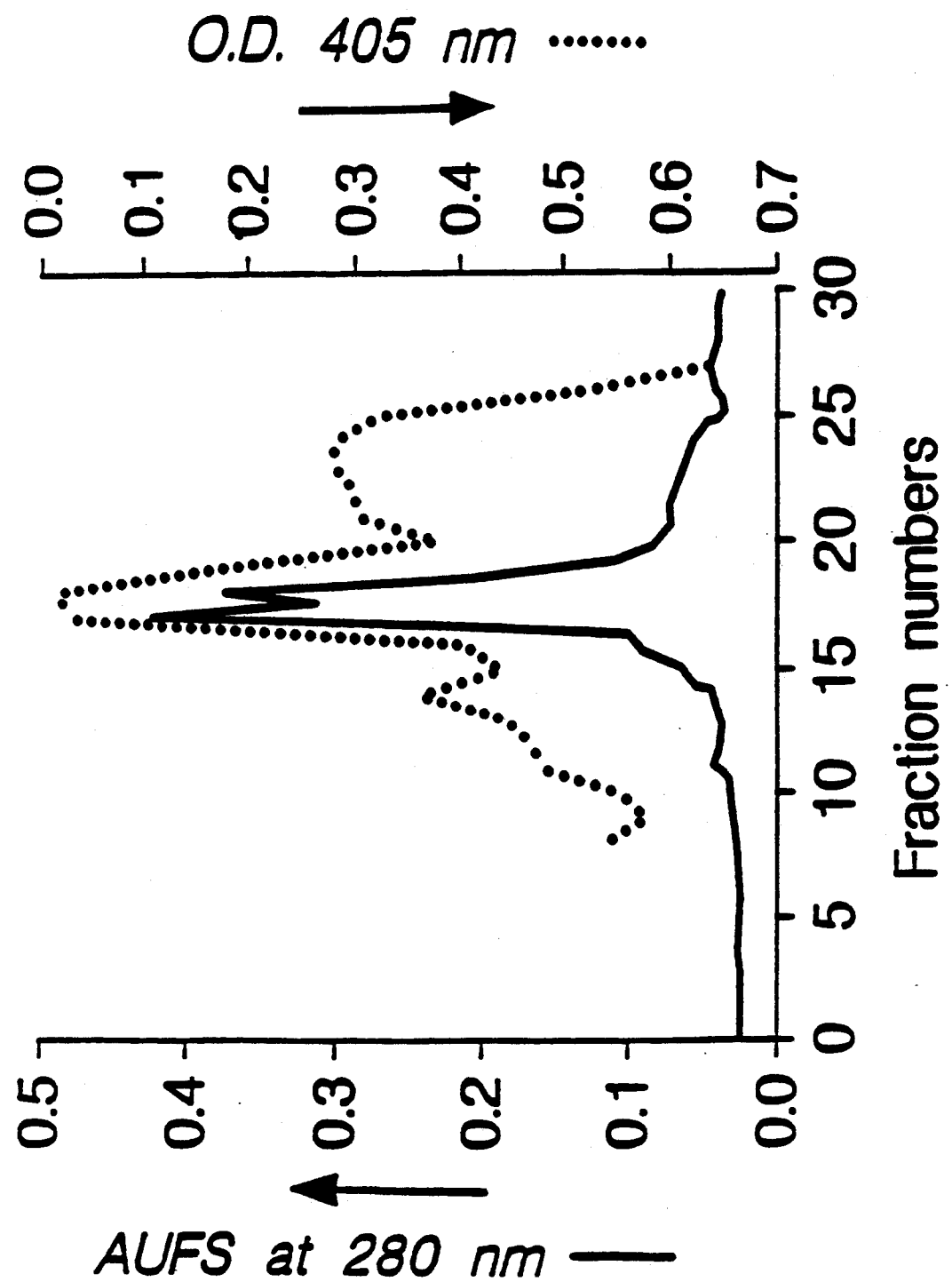
FIG. 9: A chromatogram showing a fractionated azurophile granule extract by cation exchange HPLC; the dotted line traces LPS inhibitory activity and the solid line traces protein absorbance.
Figure 10:
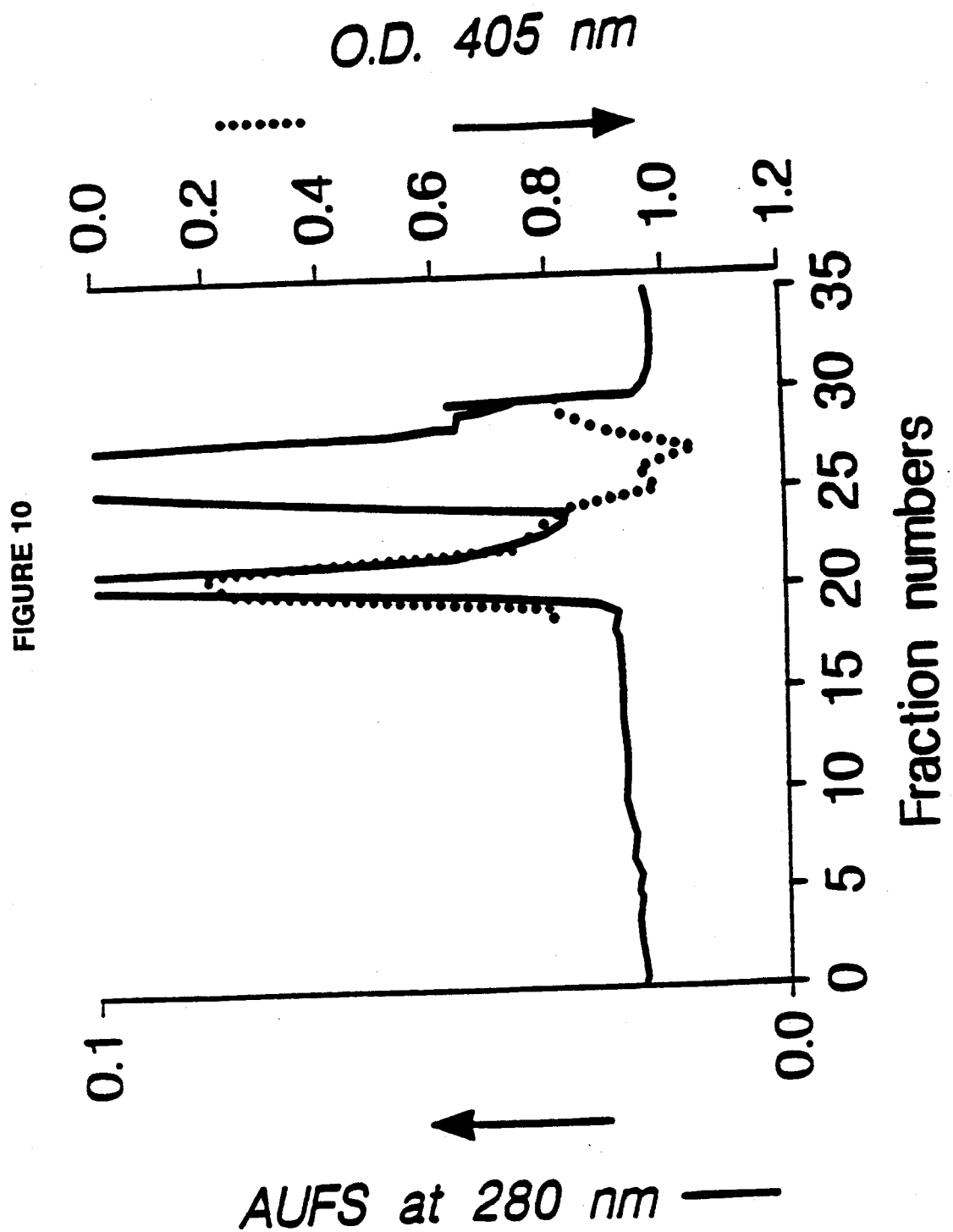
FIG. 10: A chromatogram showing a fractionated azurophile granule extract by size exclusion HPLC; the dotted line traces LPS inhibitory activity and the solid line traces protein absorbance.
Figure 11:
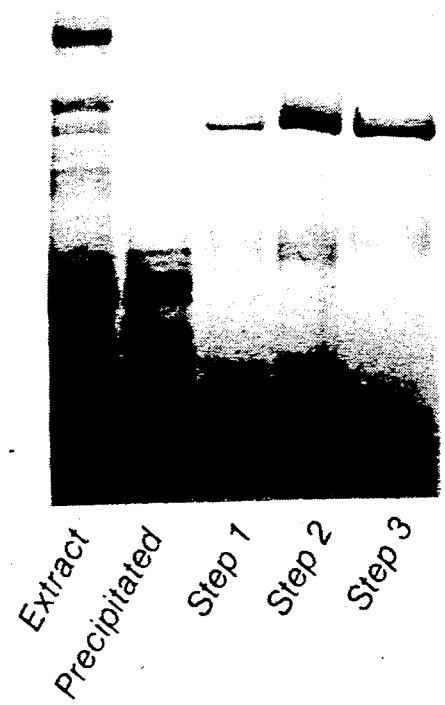
FIG. 11: An SDS-PAGE gel of the azurophil granule extract, the precipitated extract, and fraction pools from the three chromatographic steps.
Figure 12:
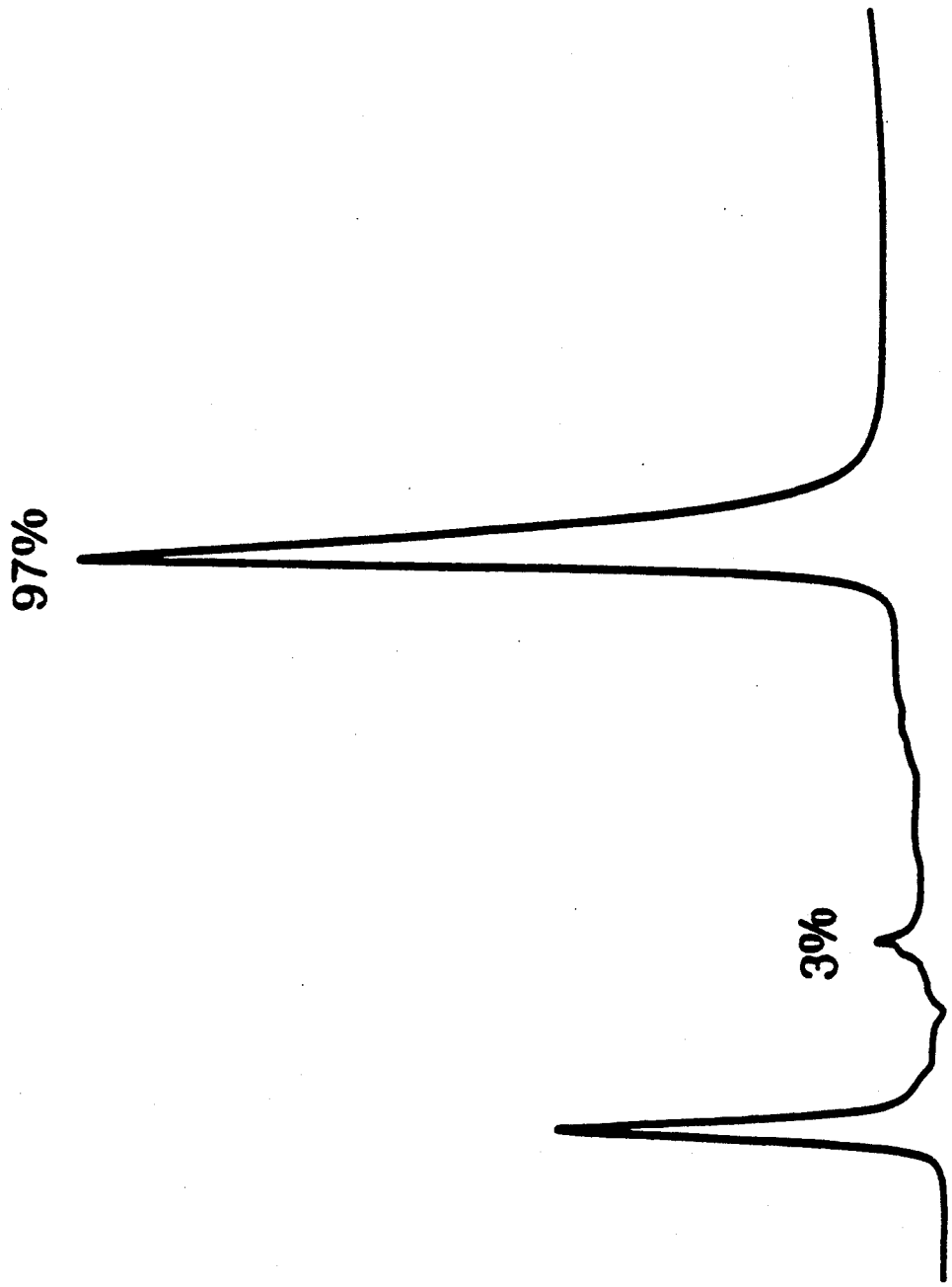
FIG. 12: Analysis of purified BPI by microbore reverse phase HPLC identifying a single major peak which accounts for 97% of the total protein.

FIGS. 8-10 show the three chromatographic steps currently employed in our lab. The absorbance is traced by the solid line and LPS inhibitory activity on the dotted lines. Table 6 shows the recovery of activity and protein and the specific activity, as measured in arbitrary LPS neutralizing units (NU). One neutralizing unit is that amount of BPI that inhibits 0.1 E.U. LPS by 50% in the LAL test. A Commassie stained SDS-PAGE gel, of these pools is shown in FIG. 11. Analysis of the purifed BPI by mirobore reverse phase HPLC (FIG. 12) identified a single major peak which accounted for 97% of the total protein by integration. As a final measure, the major reverse phase peak was collected and subjected to gas phase protein sequence analysis. The results of the analysis are expressed in bar graphs on the following pages indicating the sequence purity over the first five cycles with normal background signal delineated by a dashed line. Tryptic mapping of BPI allowed us to sequence several major fragments which further confirm the identity of the protein. The full length published sequence for BPI is known (P. W. Gray et al. (1989) *J. Biol. Chem.* 264(16):9505).

II. LPS Inhibitory Activities on BPI In Vitro

Figure 13:
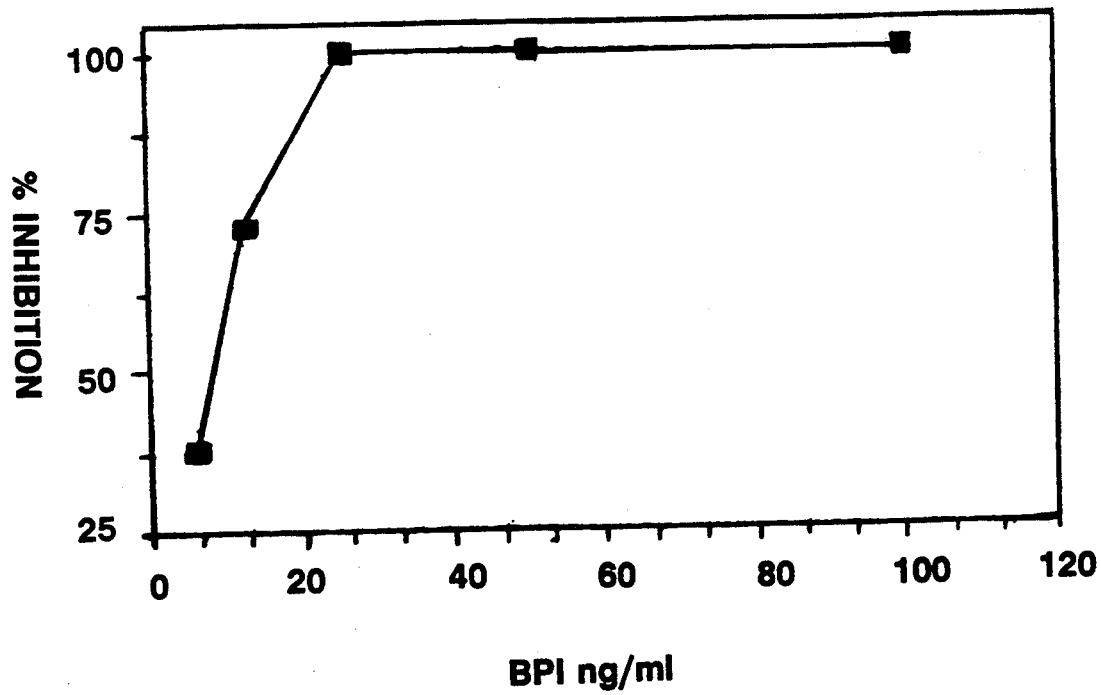
FIG. 13: A line graph illustrating inhibition of the neutrophil response to 10 ng/ml LPS by BPI.

Purification of BPI under rigorously pyrogen-free conditions, resulted in a more potent BPI preparation as shown by the dose response curve in FIG. 13. Inhibition of LPS-mediated CR upregulation was complete at 25 ng/ml BPI, representing a 4-fold increase in activity compared to the material used in example I. On a molar basis this BPI preparation inhibited LPS at approximately stoichiometric proportions, equivalent to molar inhibitory concentrations of polymyxin B. BPI also inhibited LPS-mediated TNF production by human adherent mononuclear cells at a lower concentration following purification under pyrogen-free conditions (Tables 7 and 8).

TABLE 6

| | Recovery | | Specific |
| --- | --- | --- | --- |
| | Activity | Protein | Activity |
| Extract | 100% | 100% | 0.11 NU/µg |
| Precipitated | 149% | 17.3% | 0.93 NU/µg |
| Step 1 | 35% | 1.50 | 2.51 NU/µg |
| Step 2 | 14% | 0.75 | 1.97 NU/µg |
| Step 3 | 18% | 0.10% | 18.9 NU/µg |

Figure 14:
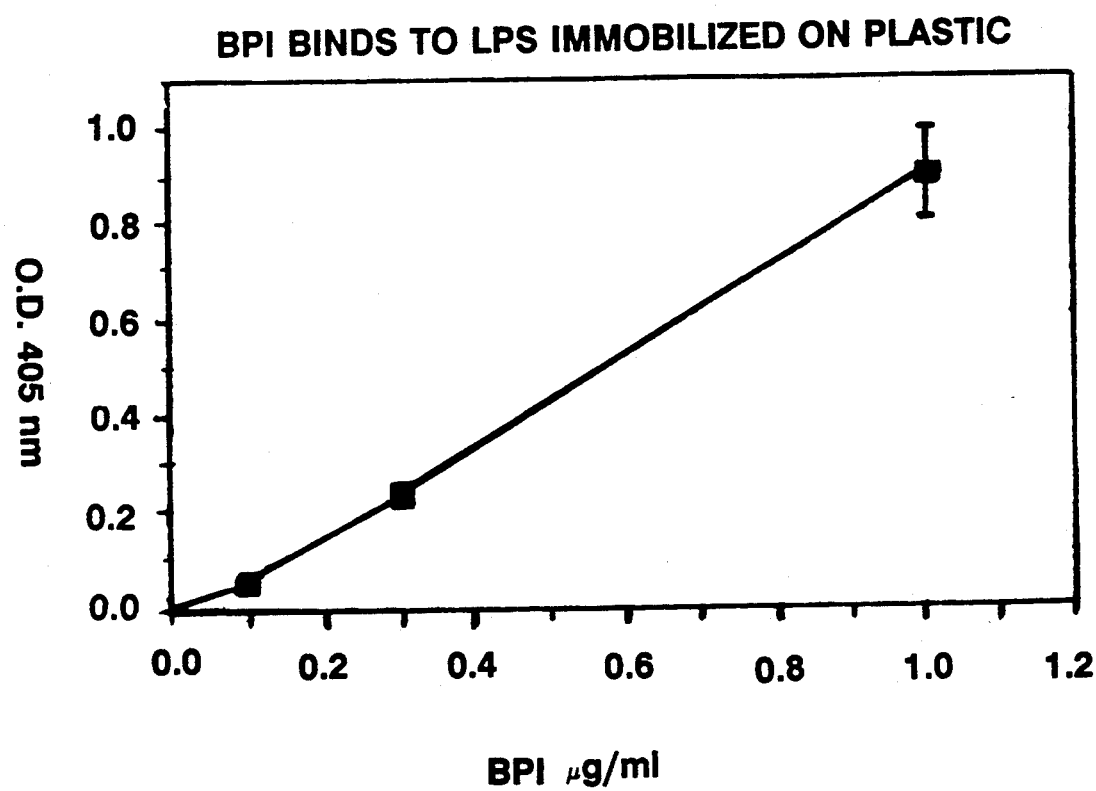
FIG. 14: A line graph showing BPI directly binds to LPS.
Figure 15:
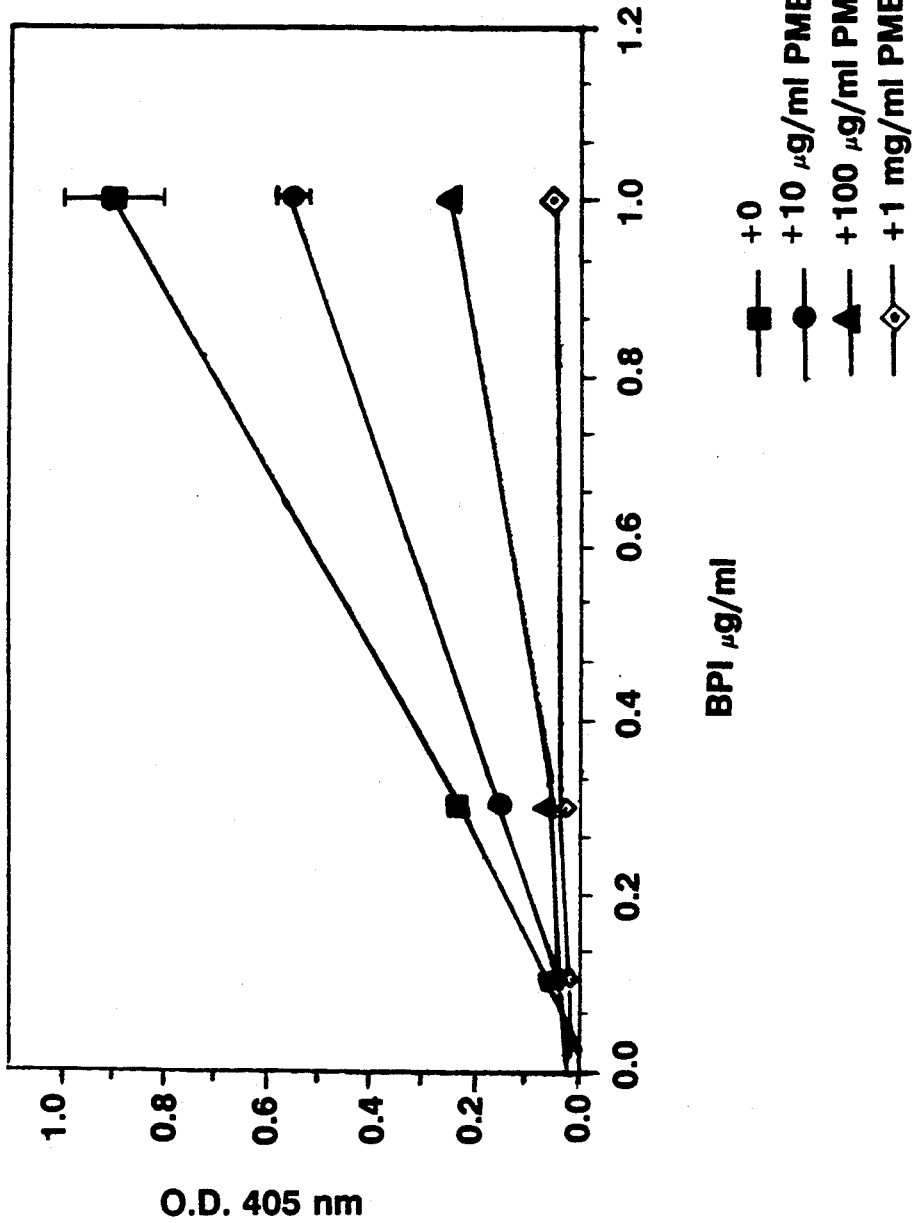
FIG. 15: A line graph showing BPI binding to immobilized LPS was inhibited by polymyxin B.
Figure 16:
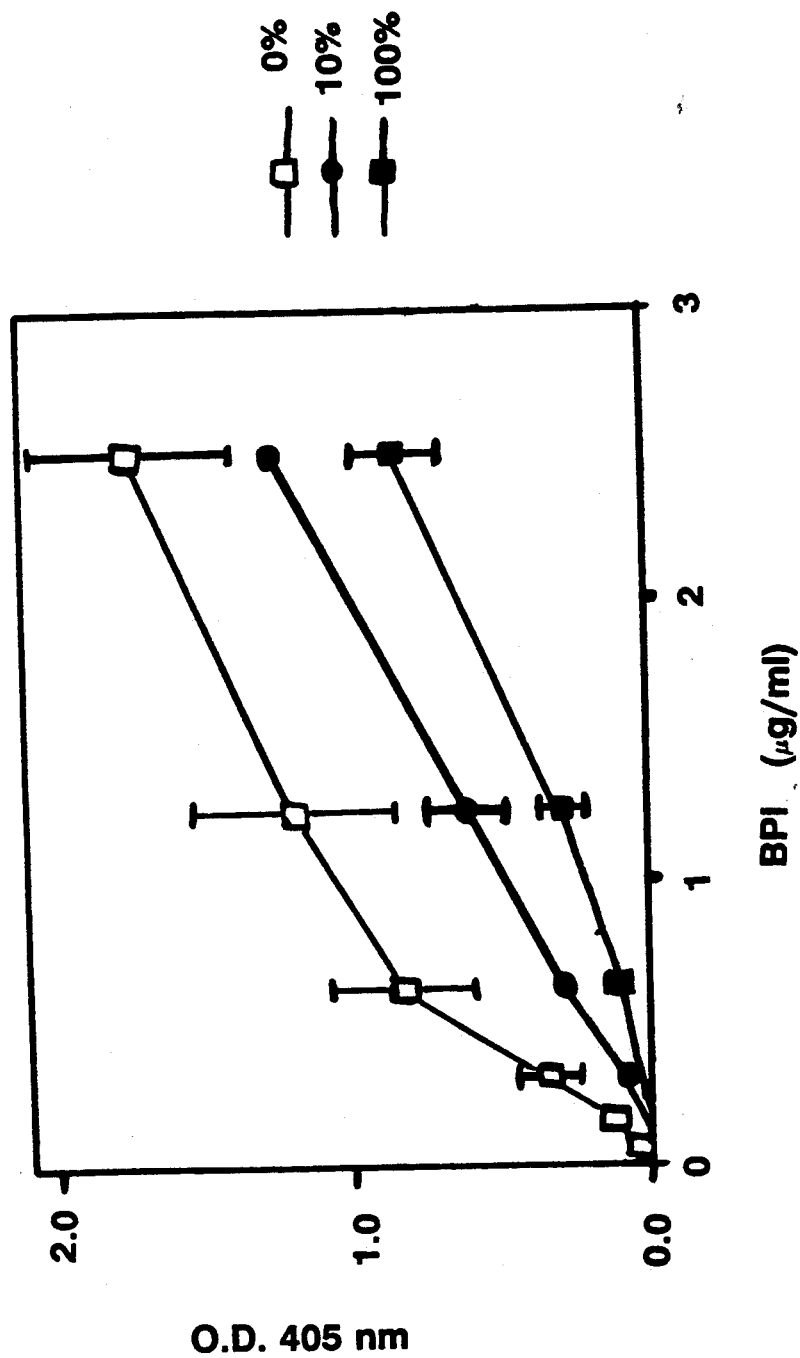
FIG. 16: A line graph showing that BPI binds to LPS in the presence of plasma.
Figure 17:
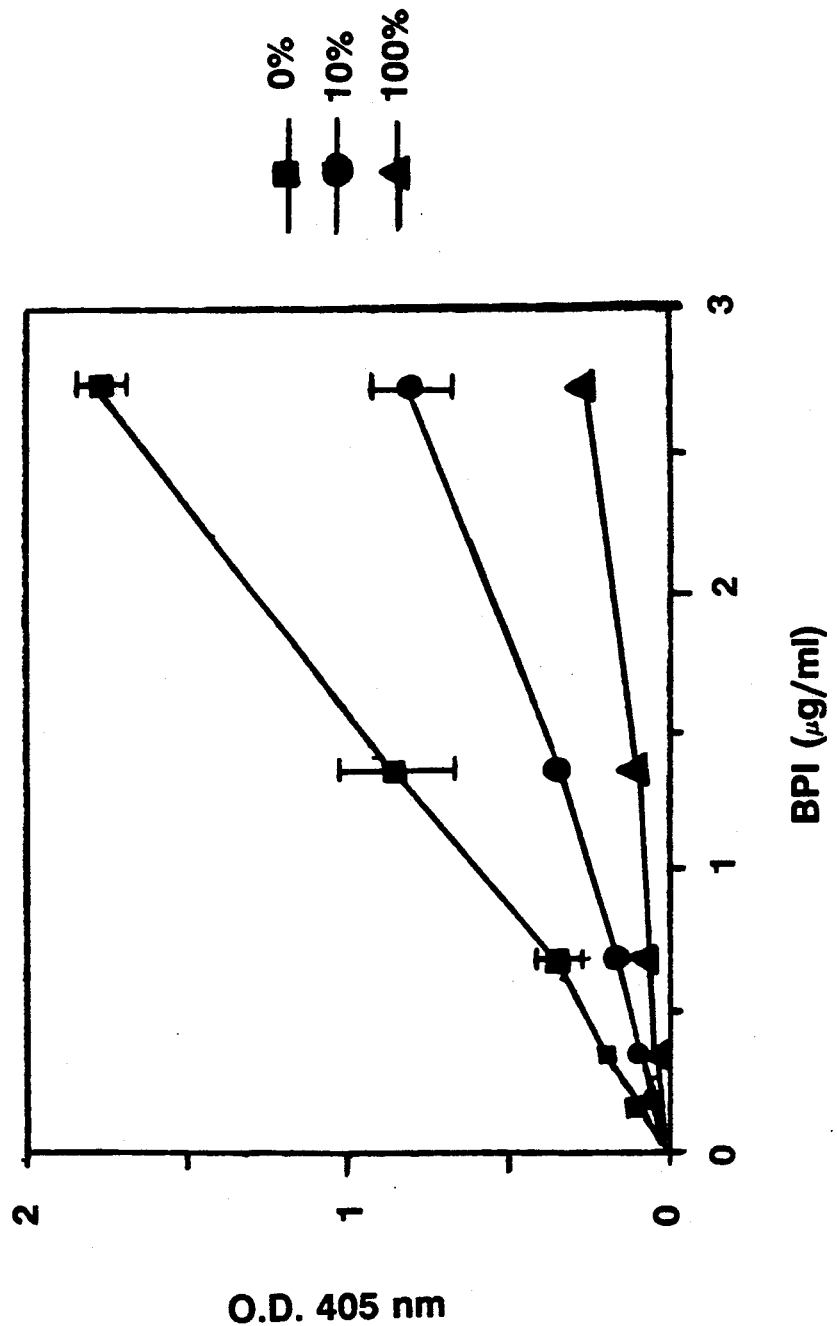
FIG. 17: A line graph showing BPI binds to LPS in the presence of serum.

BPI binds to LPS (FIG. 14). In these experiments, 4 ug of LPS/well was immobilized on 96 well plastic plates, then incubated with varying concentrations of BPI, and developed with anti-BPI polyclonal antisera. BPI binding to LPS was inhibited by polymyxin B (FIG. 15), demonstrating specificity of BPI binding. BPI binds to LPS in the presence of both plasma (FIG. 16) and serum (FIG. 17), demonstrating potential in vivo efficacy of BPI.

TABLE 7

BPI Inhibits LPS-Induced TNF Production by Human Monocytes
TNF (pg/ml) Produced in Response to LPS Preincubated with*:

| LPS ng/ml | Medium alone | 100 ng/ml PMB | 400 ng/ml BPI | 150 ng/ml BPI | 25 ng/ml BPI | Buffer Control |
| --- | --- | --- | --- | --- | --- | --- |
| 0 | 0 | 0 | 0 | 0 | 0 | 0 |
| 0.1 | 98 | 79 | 0 | 0 | 0 | 269 |
| 1 | 1150 | 1270 | 0 | 0 | 0 | 1292 |
| 10 | 1370 | 1270 | 145 | 353 | 559 | 1413 |

*E. Coli 0111:B4 LPS, was preincubated with BPI or polymyxin B (PMB), then added to adherent peripheral blood mononuclear cells.
TNF production was assayed by ELISA.

TABLE 8

INHIBITION OF LPS-INDUCED
TNF PRODUCTION BY HUMAN MONOCYTES
TNF (pg/ml) Produced in Response to LPS Preincubated with*:

| LPS | 1000 ng/ml Polymyxin B | 100 ng/ml Polymyxin B | 250 ng/ml BPI | 50 ng/ml BPI | 10 ng/ml BPI | Buffer Control |
| --- | --- | --- | --- | --- | --- | --- |
| 10 | 333 ± 18 | 601 ± 257 | 270 ± 23 | 270 ± 67 | 436 ± 38 | 697 ± 37 |
| 100 | 769 ± 101 | 1140 ± 73 | 834 ± 30 | 686 ± 84 | 1005 ± 50 | 892 ± 47 |
| 1000 | 844 ± 144 | 1016 ± 20 | 1130 ± 10 | 778 ± 189 | 1025 ± 71 | 723 ± 88 |
| S. aureus | 1685 ± 121 | 1541 ± 397 | 1558 ± 139 | 1268 ± 374 | 1554 ± 324 | 1423 ± 447 |

*BPI or polymyxin B sulfate were preincubated with 0-10 ng/ml E. Coli 0111:B4 LPS or 0.1% w/v killed S. aureus then added adherent peripheral blood mononuclear cells. TNF production was assayed by ELISA.

Example 3

BPI/Endotoxin Pyrogenicity

Stage IA—Pyrogenicity of Glycine Buffer

305 µl of Glycine Buffer control (Supplied by Redwood City) was diluted to 7 ml in PBS (Redwood City) and mixed in polypropylene tubes (pyrogen-free). The tube was labeled with notebook #1990 and tested in a three rabbit USP Rabbit Pyrogen assay at a dose of 2 ml/rabbit (actual injection dose was 2.1 ml/rabbit).

The product was non-pyrogenic; it produced a total temperature rise for all three rabbits of 0.4° C.

Stage IB–Pyrogenicity of 2 ug of BPI 304 ul of BPI (Lot 78038, dated 8/19/89) was diluted to 7 ml using PBS (Redwood City) and mixed in polypropylene tubes (pyrogen-free). The Tube was labeled with notebook #20170 and tested in a three rabbit USP Pyrogen assay at a dose of 2.0 ml/rabbit.

The product was non-pyrogenic as demonstrated by a total temperature rise of 0.2° C.

Stage II—Pyrogenicity of BPI Pre-Incubated With Endotoxin

Endotoxin from *E. Coli* 0.55.B5 (Sigma Chemicals) was diluted in PBS (Redwood City) to 4096 EU/ml. This concentration was confirmed by the LAL Assay. 304 ul of BPI (Lot 78038, dated 8/19/89) was diluted to 7 ml with the PBS diluted endotoxin (4096 EU/ml) hereinabove using polypropylene tubes. The tube was mixed by vortexing to effect mixing. The BPI+Endotoxin and Endotoxin in PBS were incubated at 37° C. in a water bath for 30 minutes. Following incubation at 37° C. the BPI+Endotoxin showed an endotoxin concentration of 122 EU/ml. The endotoxin diluted in PBS did not show a change in the end point of 4096 EU/ml.

The BPI+Endotoxin and Endotoxin in PBS in PBS were tested in the three rabbit USP pyrogen assay and were found pyrogenic with total temperature rises of 4.6° C. and 7.5° C., respectively.

Stage II (Repeat)

To achieve improved results with the manipulations of the endotoxin preparation we switched from the *E. coli* 0.55:B5 from Sigma to the Official FDA References.

A vial of EC-5 was rehydrated with PBS (Redwood City) to 2 ml to give a concentration of 5000 EU/ml. We verified by the label claim of 10,000 EU/ml by LAL assay.

The BPI+Endotoxin sample was prepared by adding 38 $\mu$l of PBI (Lot 78038) to 7.3 ml of PBS plus 320 $\mu$l of the 5000 EU/ml of EC-5 endotoxin. The preparation was mixed in a polypropylene tube (pyrogen-freed) and mixed well. An 8.0 ml sample of EC-5 -endotoxin was prepared in PBS (Redwood City) to the same concentration without the addition of BPI. Both samples was incubated at 37° C. for 30 minutes in a water bath.

Figure 18:
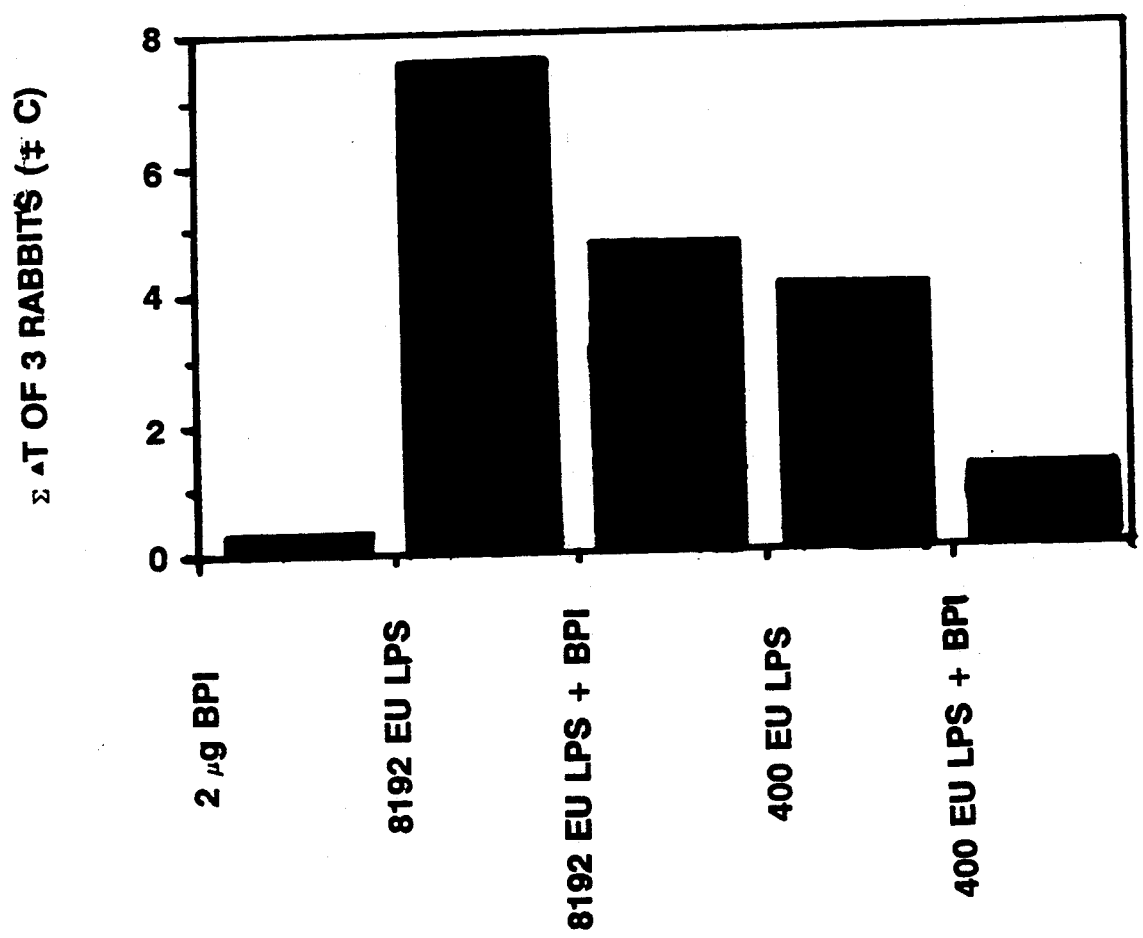
FIG. 18: A bar graph showing that BPI modulates pyrogenic response to LPS.

The two samples were tested for endotoxin activity using the LAL assay. The BPI+Endotoxin was negative. The endotoxin sample was positive at the target of 200 EU/ml (FIG. 18).

Both samples were tested in the three rabbit UPS Pyrogen Assay at a dose of 2.0 ml/rabbit.

The BPI+Endotoxin was non-pyrogenic and caused a total temperature rise of 1.1° C. The EC-5 endotoxin in PBS was pyrogenic and caused a total temperature rise of 3.9° C.

What is claimed is:

1. A method of inhibiting the pyrogenic activity of an endotoxin which comprises contacting the endotoxin with an amount of Bactericidal/Permeability Increasing Protein effective to inhibit the pyrogenic activity of the endotoxin.

2. A method of inhibiting lipopolysaccharide-mediated tumor necrosis factor production by human mononuclear cells which comprises contacting LPS with Bactericidal/Permeability Increasing Protein in an amount effective to inhibit lipopolysaccharide-mediated tumor necrosis factor production by the mononuclear cells.

3. A method of inhibiting endotoxin-mediated stimulation of neutrophils or mononuclear cells which comprises contacting endotoxin-associated lipopolysaccharide (LPS) with a purified, endotoxin-free human Bactericidal/Permeability Increasing Protein (BPI) under conditions such that the BPI binds to endotoxin-associated LPS and thereby inhibits endotoxin-mediated stimulation of neutrophils or mononuclear cells.

4. A method of treating a subject suffering from a disorder selected from the group consisting of endotoxin-related shock, endotoxin-related disseminated intravascular coagulation, endotoxin-related anemia, endotoxin-related thrombocytopenia, endotoxin-related adult respiratory distress syndrome, and endotoxin-related renal failure which comprises administering to the subject a purified, endotoxin-free, human Bactericidal/Permeability Increasing Protein under conditions such that the Bactericidal/Permeability Increasing Protein binds to endotoxin-associated lipopolysaccharide and thereby inhibits lipopolysaccharide stimulation of neutrophils and mononuclear cells so as to thereby treat the subject.

5. A method of claim 4, wherein the disorder is endotoxin-related, disseminated intravascular coagulation.

6. A method of claim 4, wherein the disorder is endotoxin-related anemia.

7. A method of claim 4, wherein the disorder is endotoxin-related leukopenia.

8. A method of claim 4, wherein the disorder is endotoxin-related thrombocytopenia.

9. A method of claim 4, wherein the disorder is endotoxin-related adult respiratory distress syndrome.

10. A method of claim 4, wherein the disorder is endotoxin-related renal failure.

11. A method of treating a subject suffering from endotoxin-related shock which comprises administering to the subject a purified, endotoxin-free, human Bactericidal/Permeability Increasing Protein under conditions such that the Bactericidal/Permeability Increasing Protein binds to endotoxin-associated lipopolysaccharide and inhibits endotoxin-related shock so as to thereby treat the subject.

12. A method of reducing the symptoms associated with a disorder which comprises administering to a subject in need thereof purified, endotoxin-free Bactericidal/Permeability Increasing Protein under conditions such that the Bactericidal/Permeability Increasing Protein binds to endotoxin-associated lipopolysaccharide and inhibits lipopolysaccharide stimulation of neutrophils and mononuclear cells so as to thereby reduce the symptoms associated with the disorder, the disorder being selected from the group consisting of endotoxin-related shock, endotoxin-related disseminated intravascular coagulation, endotoxin-related anemia, endotoxin-related leukopenia, endotoxin-related thrombocytopenia, endotoxin-related adult respiratory distress syndrome, and endotoxin-related renal failure.

13. A method of claim 12, wherein the disorder is endotoxin-related shock.

14. A method of claim 12, wherein the disorder is endotoxin-related, disseminated intravascular coagulation.

15. A method of claim 12, wherein the disorder is endotoxin-related anemia.

16. A method of claim 12, wherein the disorder is endotoxin-related leukopenia.

17. A method of claim 12, wherein the disorder is endotoxin-related thrombocytopenia.

18. A method of claim 12, wherein the disorder is endotoxin-related adult respiratory distress syndrome.

19. A method of claim 12, wherein the disorder is endotoxin-related renal failure.

20. A method of recovering a purified, endotoxin-free, human Bactericidal/Permeability Increasing Protein having enhanced activity to inhibit endotoxin-mediated stimulation of neutrophils and mononuclear cells which comprises:

a) obtaining a sample containing Bactericidal/Permeability Increasing Protein;
   b) subjecting the sample so obtained to chromatography so as to obtain the endotoxin-free, human Bactericidal/Permeability Increasing Protein separate from other substances present in the sample; and
   c) recovering the purified, endotoxin-free, human Bactericidal/Permeability Increasing Protein having enhanced activity to inhibit endotoxin-mediated stimulation of neutrophils and mononuclear cells.

21. A method of claim 20, wherein the Bactericidal/Permeability Increasing Protein comprises native BPI.

22. A method of claim 20, wherein the Bactericidal/Permeability Increasing Protein comprises a biologically active polypeptide analog of BPI.

23. A method of claim 22, wherein the biologically active polypeptide analog of BPI comprises a polypeptide which has a molecular weight of about 25 kD and corresponds to the N-terminal amino acid sequence of BPI.

24. A method of claim 3, wherein the Bactericidal/-Permeability Increasing Protein comprises recombinant Bactericidal/Permeability Increasing Protein or a biologically active polypeptide analog thereof.

25. A method of claim 24, wherein the biologically active polypeptide analog of Bactercidal/Permeability Increasing Protein comprises a polypeptide which has a molecular weight of about 25 kD and corresponds to the N-terminal amino acid sequence of BPI.

* * * * *